(12) United States Patent
Hareland et al.

(10) Patent No.: US 10,722,717 B2
(45) Date of Patent: Jul. 28, 2020

(54) DETECTING AND RESPONDING TO ANTI-TACHYARRHYTHMIA SHOCKS

(71) Applicant: Medtronic, Inc., Minneapolis, MN (US)

(72) Inventors: Scott A. Hareland, Lino Lakes, MN (US); James D. Reinke, Maple Grove, MN (US); Jon D. Schell, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 179 days.

(21) Appl. No.: 15/910,032

(22) Filed: Mar. 2, 2018

(65) Prior Publication Data
US 2018/0185640 A1    Jul. 5, 2018

Related U.S. Application Data

(62) Division of application No. 15/141,758, filed on Apr. 28, 2016, now Pat. No. 10,232,182.

(51) Int. Cl.
*A61N 1/36*    (2006.01)
*A61N 1/365*    (2006.01)
(Continued)

(52) U.S. Cl.
CPC ............ *A61N 1/365* (2013.01); *A61N 1/056* (2013.01); *A61N 1/3621* (2013.01);
(Continued)

(58) Field of Classification Search
CPC .... A61N 1/365; A61N 1/3962; A61N 1/3756; A61N 1/37288; A61N 1/3712; A61N 1/056; A61N 1/3621
See application file for complete search history.

(56) References Cited

U.S. PATENT DOCUMENTS 5,117,824 A    6/1992 Keimel et al.
5,545,186 A    8/1996 Olson et al.
(Continued)

OTHER PUBLICATIONS (PCT/US2017/029562) PCT Notification of Transmittal of the International Search Report and the Written Opinion of the International Searching Authority, dated Jul. 14, 2017, 9 pages.
(Continued)

*Primary Examiner* — Rex R Holmes

(57) ABSTRACT

In some examples, an implantable medical device determines that another medical device delivered an anti-tachyarrhythmia shock, and delivers post-shock pacing in response to the determination. The implantable medical device may be configured to both detect the delivery of the shock in a sensed electrical signal and, if delivery of the shock is not detected, determine that the shock was delivered based on detection of asystole of the heart. The asystole may be detected based on the sensed electrical signal. In some examples, an implantable medical device is configured to revert from a post-shock pacing mode to a baseline pacing mode by iteratively testing a plurality of decreasing values of pacing pulse magnitude until loss of capture is detected. The implantable medical device may update a baseline value of the pacing pulse magnitude for the baseline mode based on the detection of loss of capture.

16 Claims, 9 Drawing Sheets

(51) Int. Cl.
*A61N 1/362* (2006.01)
*A61N 1/05* (2006.01)
*A61N 1/37* (2006.01)
*A61N 1/372* (2006.01)
*A61N 1/375* (2006.01)
*A61N 1/39* (2006.01)

(52) U.S. Cl.
CPC ......... *A61N 1/3712* (2013.01); *A61N 1/3756* (2013.01); *A61N 1/37288* (2013.01); *A61N 1/3962* (2013.01)

(56) References Cited

U.S. PATENT DOCUMENTS

| | | | |
|---|---|---|---|
| 5,755,736 | A | 5/1998 | Gillberg et al. |
| 5,772,692 | A | 6/1998 | Armstrong |
| 6,892,094 | B2 | 5/2005 | Ousdigian et al. |
| 7,162,298 | B2 | 1/2007 | Ideker et al. |
| 7,392,081 | B2 | 6/2008 | Wagner et al. |
| 8,744,572 | B1 | 6/2014 | Greenhut et al. |
| 9,278,229 | B1 * | 3/2016 | Reinke ................. A61N 1/3937 |
| 10,232,182 | B2 | 3/2019 | Hareland et al. |
| 2010/0069986 | A1 | 3/2010 | Stahl et al. |
| 2012/0101543 | A1 | 4/2012 | Demmer et al. |
| 2014/0135867 | A1 | 5/2014 | Demmer et al. |
| 2014/0214104 | A1 | 7/2014 | Greenhut et al. |
| 2015/0246235 | A1 | 9/2015 | Ghosh |
| 2015/0321011 | A1 | 11/2015 | Carney et al. |

OTHER PUBLICATIONS

Prosecution History from U.S. Appl. No. 15/141,758, dated Jan. 11, 2018 through Jun. 12, 2018, 52 pages.
International Preliminary Report on Patentability from International Application No. PCT/US2017/029562, dated Oct. 30, 2018, 7 pages.
Communication Pursuant to Rules 161(1) and 162 EPC dated Dec. 5, 2018 from counterpart European Application No. 17724150.2, 3 pages.
Response to Communication Pursuant to Rules 161(1) and 162 EPC dated Dec. 5, 2018 from counterpart European Application No. 17724150.2, filed Jun. 4, 2019, 13 pages.
Notice of Intent to Grant and Text Intended to Grant from counterpart European Application No. 17724150.2, dated Sep. 9, 2019, 99 pages.

* cited by examiner

DETECTING AND RESPONDING TO ANTI-TACHYARRHYTHMIA SHOCKS

This application is a divisional of U.S. patent application Ser. No. 15/141,758, which was filed on Apr. 28, 2016 and issued as U.S. Pat. No. 10,232,182 on Mar. 19, 2019, the entire content of which is incorporated herein by reference in its entirety.

TECHNICAL FIELD

The disclosure relates generally to medical devices and, more particularly, medical devices configured to deliver post-shock pacing after delivery of an anti-tachyarrhythmia shock.

BACKGROUND

Implantable medical devices (IMDs), including implantable pacemakers and implantable cardioverter-defibrillators (ICDs), record cardiac electrogram (EGM) signals for sensing cardiac events, e.g., P-waves and R-waves. IMDs detect episodes of bradycardia, tachycardia and/or fibrillation from the sensed cardiac events, and respond to the episodes as needed with pacing therapy or high-voltage anti-tachyarrhythmia shocks, e.g., cardioversion or defibrillation shocks. Types of pacing therapy include bradycardia pacing, cardiac resynchronization therapy (CRT), anti-tachycardia pacing (ATP), which may attempted prior to resorting to an anti-tachyarrhythmia shock to terminate a tachyarrhythmia, and post-shock pacing, which may be delivered to help the heart recover from successful termination of a tachyarrhythmia by an anti-tachyarrhythmia shock.

Some IMDs include a can or housing that is implanted subcutaneously or submuscularly, and coupled to one or more intracardiac leads. Such IMDs may be capable of providing cardiac pacing and/or anti-tachyarrhythmia shock therapies via the one or more leads. However, other IMD configurations that avoid the use of intracardiac leads have been proposed. For example, an intracardiac pacing device (IPD) may be fully implantable within the heart, i.e., may include a housing and electrodes configured to be implanted in the heart. The IPD may be configured to deliver one or more types of pacing.

As another example, an extracardiovascular ICD system may include a can or housing that is implanted at a subcutaneous or submuscular location, and at least one lead implanted extracardiovascularly, e.g., subcutaneously or substernally. Extracardiovascular ICD systems deliver anti-tachyarrhythmia shocks, and may also be configured to deliver pacing pulses, using one or more electrodes on the lead and/or housing. However, the greater distance between the electrodes and the cardiac tissue, e.g., relative to the electrodes of an intracardiac lead or IPD, may necessitate greater pacing pulse magnitudes to capture the heart. Consequently, co-implantation of an extracardiovascular ICD system and IPD to provide shock and pacing therapies, respectively, has been proposed.

SUMMARY

In general, this disclosure is directed to techniques related to delivery of post-shock pacing. In some examples, the techniques enable an IMD, e.g., an IPD, to determine whether another medical device, e.g., an extracardiovascular ICD system, delivered an anti-tachyarrhythmia shock. Determining whether the other device delivered the shock may, for example, facilitate delivery of post-shock pacing in response to successful termination of a tachyarrhythmia by the shock.

The IMD is configured to determine whether the other medical device delivered the shock without communicating with the other medical device. The IMD may be configured to both detect the delivery of the shock in a sensed electrical signal and, if delivery of the shock is not detected, determine that the shock was delivered based on detection of asystole of the heart. The IMD may detect the asystole based on the sensed electrical signal, e.g., based on not detecting a cardiac depolarization within the signal for a threshold period of time. In this manner, the IMD may be able to provide post-shock pacing after an anti-tachyarrhythmia shock delivered by another medical device has terminated a tachyarrhythmia without receiving a communication indicating delivery of the shock from the other device, and in situations where the shock may not be reliably detected.

In some examples, an IMD. e.g., an IPD, is configured to revert from a post-shock pacing mode to a baseline pacing mode by iteratively testing decreasing values of pacing pulse magnitude until loss of capture is detected. The IMD may update a baseline value of the pacing pulse magnitude for the baseline mode based on the detection of loss of capture. The baseline pacing mode may be, for example, a bradycardia pacing mode. If one or more pulses at an initial reversion amplitude fail to capture the heart, the IMD may suspend reversion and continue to deliver post-shock pacing, e.g., for a period of time. In this manner, the IMD may revert to the baseline pacing mode at a time when the heart is ready for revision, and identify a baseline pacing magnitude suitable for the post-shock condition of the heart.

In one example, a method for an implantable medical device to revert from a post-shock pacing mode to a baseline pacing mode, wherein the baseline pacing mode specifies a baseline value of a pacing pulse magnitude, and the post-shock pacing mode specifies a post-shock value of the pacing pulse magnitude that is greater than the baseline value, the method comprises iteratively testing, by the implantable medical device delivering a plurality of pacing pulses to a heart of a patient, a plurality of values of the pacing pulse magnitude that decrease from an initial reversion value that is greater than the baseline value and less than the post-shock value. The method further comprises determining, by the implantable medical device, whether each of the plurality of values of the pacing pulse magnitude captures the heart and in response to determining that one of the plurality of values of the pacing pulse magnitude failed to capture the heart, updating, by the implantable medical device, the baseline value of the pacing pulse magnitude, and delivering, by the implantable medical device, pacing pulses having the updated baseline value of the pacing pulse magnitude according to the baseline pacing mode.

In another example, an implantable medical device comprises therapy delivery circuitry configured to deliver pacing pulses to a heart of a patient via a plurality of electrodes. The implantable medical device further comprises a memory configured to store a baseline value of a pacing pulse magnitude for delivery of pacing pulses according to a baseline pacing mode, a post-shock value of the pacing pulse magnitude for delivery of pacing pulses according to a post-shock pacing mode, wherein the post-shock value of the pacing pulse magnitude is greater than the baseline value, and an initial reversion value of the pacing pulse magnitude that is greater than the baseline value and less than the post-shock value. The implantable medical device further comprises processing circuitry configured to revert the implantable medical device from the post-shock pacing mode to the baseline pacing mode by at least: controlling the therapy delivery circuitry to deliver a plurality of pacing pulses to the heart to iteratively test a plurality of values of the pacing pulse magnitude that decrease from the initial reversion value; determining whether each of the plurality of values of the pacing pulse magnitude captured the heart; and in response to determining that one of the plurality of values of the pacing pulse magnitude failed to capture the heart: updating the baseline value of the pacing pulse magnitude; and controlling the therapy delivery circuitry to deliver pacing pulses having the updated baseline value of the pacing pulse magnitude according to the baseline pacing mode.

In another example, a method comprises sensing, by an implantable medical device, an electrical signal via a plurality of electrodes, determining, by the implantable medical device, that an amplitude of the electrical signal is above an anti-tachyarrhythmia shock threshold, and detecting, by the implantable medical device, delivery of a first anti-tachyarrhythmia shock by another medical device based on the determination. The method further comprises detecting, by the implantable medical device, asystole of the heart based on the electrical signal, and determining, by the implantable medical device, that the other medical device delivered a second anti-tachyarrhythmia shock based on the detection of asystole.

In another example, an implantable medical device comprises sensing circuitry configured to sense an electrical signal via a plurality of electrodes, and processing circuitry. The processing circuitry is configured to determine that an amplitude of the electrical signal is above an anti-tachyarrhythmia shock threshold, and detect delivery of an anti-tachyarrhythmia shock by another medical device based on the determination. The processing circuitry is further configured to detect asystole of the heart based on the electrical signal, and determine, without detecting the delivery of the anti-tachyarrhythmia shock, that the other medical device delivered the anti-tachyarrhythmia shock based on the detection of asystole.

In another example, an implantable medical device comprises therapy delivery circuitry configured to deliver pacing pulses to a heart of a patient via a plurality of electrodes, and sensing circuitry configured to sense an electrical signal via the plurality of electrodes. The implantable medical device further comprises a memory configured to store a baseline value of a pacing pulse magnitude for delivery of pacing pulses according to a baseline pacing mode, a post-shock value of the pacing pulse magnitude for delivery of pacing pulses according to a post-shock pacing mode, wherein the post-shock value of the pacing pulse magnitude is greater than the baseline value, and an initial reversion value of the pacing pulse magnitude that is greater than the baseline value and less than the post-shock value. The implantable medical device further comprises processing circuitry configured to control the therapy delivery circuitry to deliver pacing pulses having the baseline value of the pacing pulse magnitude according to the baseline pacing mode. The processing circuitry is further configured to determine that an amplitude of the electrical signal is above an anti-tachyarrhythmia shock threshold, and detect delivery of an anti-tachyarrhythmia shock by another medical device based on the determination. The processing circuitry is further configured to detect asystole of the heart based on the electrical signal, and determine, without detecting the delivery of the anti-tachyarrhythmia shock, that the other medical device delivered the anti-tachyarrhythmia shock based on the detection of asystole. The processing circuitry is further configured to, in response to either detecting the delivery of the anti-tachyarrhythmia shock by another medical device or determining, without detecting the delivery of the anti-tachyarrhythmia shock, that the other medical device delivered the anti-tachyarrhythmia shock, control the therapy delivery circuitry to switch to delivery of pacing pulses having the post-shock value of the pacing pulse magnitude according to the post-shock pacing mode. The processing circuitry is further configured to revert the implantable medical device from the post-shock pacing mode to the baseline pacing mode by at least controlling the therapy delivery circuitry to deliver a plurality of pacing pulses to the heart to iteratively test a plurality of values of the pacing pulse magnitude that decrease from the initial reversion value; determining whether each of the plurality of values of the pacing pulse magnitude captured the heart; and in response to determining that one of the plurality of values of the pacing pulse magnitude failed to capture the heart: updating the baseline value of the pacing pulse magnitude, and controlling the therapy delivery) circuitry to deliver pacing pulses having the updated baseline value of the pacing pulse magnitude according to the baseline pacing mode.

In other examples, non-transitory computer-readable media comprise program instructions that, when executed by one or more programmable processors, cause the one or more programmable processors to perform any of the methods or techniques described herein.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

In general, this disclosure describes example techniques related to delivery of post-shock pacing, including techniques for determining whether another medical device delivered an anti-tachyarrhythmia shock, and for reverting from a post-shock pacing mode to a baseline, e.g., bradycardia, pacing mode. In the following description, references are made to illustrative examples. It is understood that other examples may be utilized without departing from the scope of the disclosure.

Figure 1A:
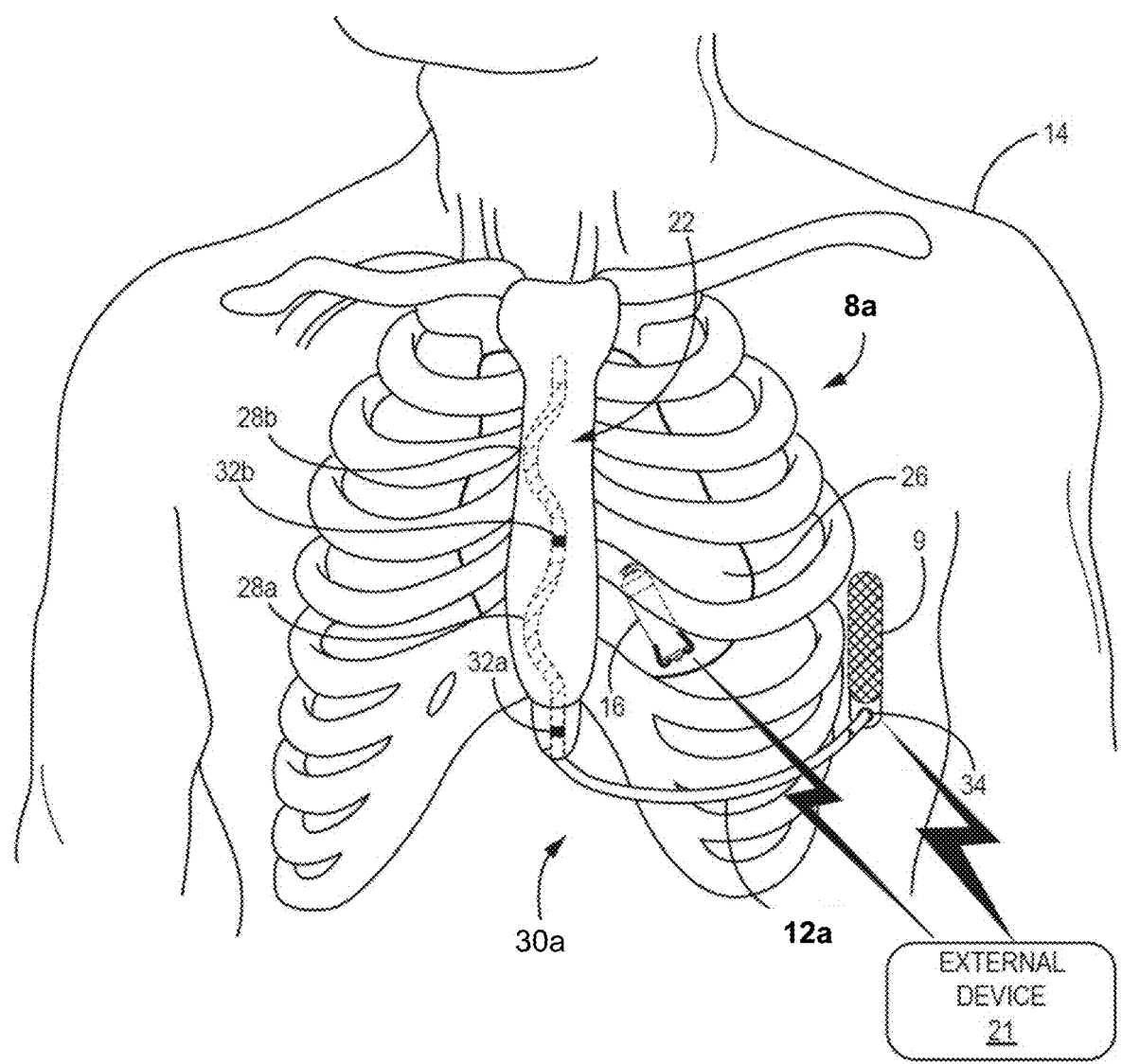
FIG. 1A-1C are front, side, and transverse views, respectively, of an example medical device system that includes an extracardiovascular ICD system and an IPD implanted within a patient.
Figure 1B:
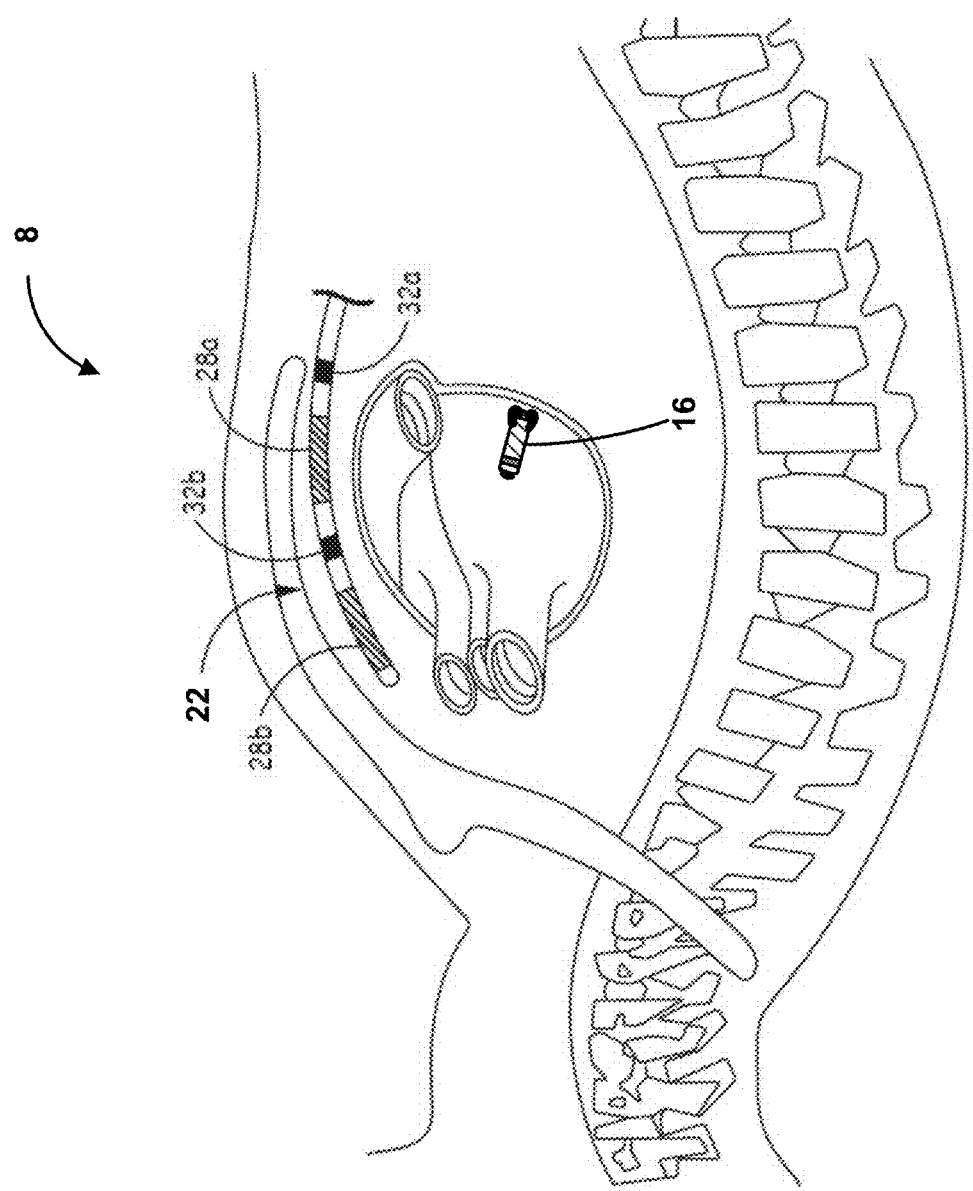
Figure 1C:
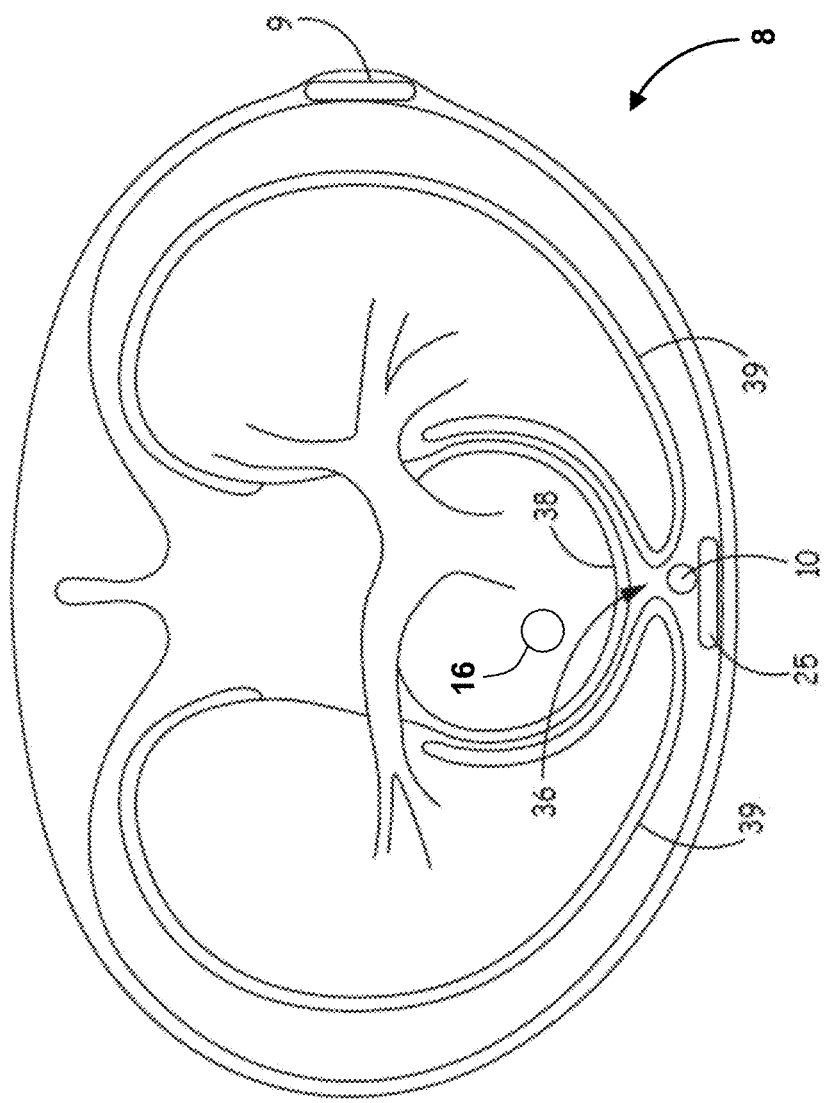

FIG. 1A, FIG. 1B, and FIG. 1C are conceptual diagrams illustrating various views of an example implantable medical device (IMD) system 8a implanted within a patient 14. IMD system 8a includes an extracardiovascular ICD system 30a implanted in patient 14, and an intracardiac pacing device (IPD) 16 implanted within heart 26 of patient 14. FIG. 1A is a front view of IMD system 8 and patient 14. FIG. 1B is a side view of IMD system 8 and patient 14. FIG. 1C is a transverse view of IMD system 8 and patient 14.

Referring to FIG. 1A, ICD system 30a includes an implantable cardiac defibrillator (ICD) 9 connected to at least one implantable cardiac defibrillation lead 12a. ICD 9 is configured to deliver high-energy cardioversion or defibrillation pulses to a patient's heart when atrial or ventricular fibrillation is detected. Cardioversion shocks are typically delivered in synchrony with a detected R-wave when fibrillation detection criteria are met. Defibrillation pulses are typically delivered when fibrillation criteria are met, and the R-wave cannot be discerned from signals sensed by ICD 9.

ICD 9 of FIG. 1A is implanted subcutaneously or submuscularly on the left side of patient 14 above the ribcage. Defibrillation lead 12a may be implanted at least partially in a substernal location, e.g., between the ribcage and/or sternum 22 and heart 26. In one such configuration, a proximal portion of lead 12a extends subcutaneously from ICD 9 toward sternum 22 and a distal portion of lead 12a extends superior under or below the sternum 22 in the anterior mediastinum 36. The anterior mediastinum 36 is bounded laterally by the pleurae 39 (see FIG. 1C), posteriorly by the pericardium, and anteriorly by the sternum 22. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 12a extends along the posterior side of the sternum 22 substantially within the loose connective tissue and/or substernal musculature of the anterior mediastinum. Lead 12a may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 22 or ribcage.

In other examples, lead 12a may be implanted at other extracardiovascular locations. For example, defibrillation lead 12a may extend subcutaneously above the ribcage from ICD 9 toward a center of the torso of patient 14, bend or turn near the center of the torso, and extend subcutaneously superior above the ribcage and/or sternum 22. Defibrillation lead 12a may be offset laterally to the left or the right of the sternum 22 or located over the sternum 22. Defibrillation lead 12a may extend substantially parallel to the sternum 22 or be angled lateral from the sternum 22 at either the proximal or distal end.

Defibrillation lead 12a includes an insulative lead body having a proximal end that includes a connector 34 configured to be connected to ICD 9 and a distal portion that includes one or more electrodes. Defibrillation lead 12a also includes one or more conductors that form an electrically conductive path within the lead body and interconnect the electrical connector and respective ones of the electrodes.

Defibrillation lead 12a includes a defibrillation electrode that includes two sections or segments 28a and 28b, collectively (or alternatively) defibrillation electrode 28. The defibrillation electrode 28 is toward the distal portion of defibrillation lead 12a. e.g., toward the portion of defibrillation lead 12a extending along the sternum 22. Defibrillation lead 12a is placed below and/or along sternum 22 such that a therapy vector between defibrillation electrodes 28a or 28b and a housing electrode formed by or on ICD 9 (or other second electrode of the therapy vector) is substantially across a ventricle of heart 26. The therapy vector may, in one example, be viewed as a line that extends from a point on defibrillation electrode 28 (e.g., a center of one of the defibrillation electrode sections 28a or 28b) to a point on the housing electrode of ICD 9. Defibrillation electrode 28 may, in one example, be an elongated coil electrode.

Defibrillation lead 12a may also include one or more sensing electrodes, such as sensing electrodes 32a and 32b (individually or collectively, "sensing electrode(s) 32"), located along the distal portion of defibrillation lead 12a. In the example illustrated in FIG. 1A and FIG. 1B, sensing electrodes 32a and 32b are separated from one another by defibrillation electrode 28a. In other examples, however, sensing electrodes 32a and 32b may be both distal of defibrillation electrode 28 or both proximal of defibrillation electrode 28. In other examples, lead 12a may include more or fewer electrodes at various locations proximal and/or distal to defibrillation electrode 28. In the same or different examples, ICD 9 may include one or more electrodes on another lead (not shown).

ICD system 30a may sense electrical signals via one or more sensing vectors that include combinations of electrodes 32a and 32b and the housing electrode of ICD 9. In some instances, ICD 9 may sense cardiac electrical signals using a sensing vector that includes one of the defibrillation electrode sections 28a and 28b and one of sensing electrodes 32a and 32b or the housing electrode of ICD 9. The sensed electrical intrinsic signals may include electrical signals generated by cardiac muscle and indicative of depolarizations and repolarizations of heart 26 at various times during the cardiac cycle. ICD 9 analyzes the electrical signals sensed by the one or more sensing vectors to detect tachyarrhythmia, such as ventricular tachycardia or ventricular fibrillation. In response to detecting the tachyarrhythmia, ICD 9 may begin to charge a storage element, such as a bank of one or more capacitors, and, when charged, deliver one or more defibrillation pulses via defibrillation electrode 28 of defibrillation lead 12a if the tachyarrhythmia is still present.

In the example of FIG. 1A, IPD 16 is implanted within the right ventricle of heart 26 to sense electrical activity of heart 26 and deliver pacing therapy, e.g., anti-tachycardia pacing (ATP) therapy, bradycardia pacing therapy, and/or post-shock pacing, to heart 26. IPD 16 may be attached to an interior wall of the right ventricle of heart 26 via one or more fixation elements that penetrate the tissue. These fixation elements may secure IPD 16 to the cardiac tissue and retain an electrode (e.g., a cathode or an anode) in contact with the cardiac tissue. However, in other examples, system 8 may include additional pacing devices 16 within respective chambers of heart 26 (e.g., right or left atrium and/or left ventricle). In further examples, IPD 16 may be attached to an external surface of heart 26 (e.g., in contact with the epicardium) such that IPD 16 is disposed outside of heart 26.

IPD 16 may be capable sensing electrical signals using the electrodes carried on the housing of IPD 16. These electrical signals may be electrical signals generated by cardiac muscle and indicative of depolarizations and repolarizations of heart 26 at various times during the cardiac cycle. IPD 16 may analyze the sensed electrical signals to detect bradycardia and tachyarrhythmias, such as ventricular tachycardia or ventricular fibrillation. In response to detecting the bradycardia, IPD 16 may deliver bradycardia pacing via the electrodes of IPD 16. In response to detecting tachyarrhythmia, IPD 16 may, e.g., depending on the type of tachyarrhythmia, deliver ATP therapy via the electrodes of IPD 16. In some examples, as described in greater detail herein, IPD 16 may additionally or alternatively deliver post-shock pacing in response to determining that another medical device, e.g., ICD system 30a, delivered an anti-tachyarrhythmia shock.

IPD 16 and ICD system 30a may be configured to operate completely independently of one another. In such a case, IPD 16 and ICD system 30a are not capable of establishing telemetry communication sessions with one another to exchange information about sensing and/or therapy using one-way or two-way communication. Instead, each of IPD 16 and ICD system 30a analyze the data sensed via their respective electrodes to make tachyarrhythmia detection and/or therapy decisions. As such, each device does not know if the other will detect the tachyarrhythmia, if or when it will provide therapy, and the like.

During a tachyarrhythmia that could be treated with either ATP or an anti-tachyarrhythmia shock, it may be preferred that anti-tachyarrhythmia therapies do not overlap or that ATP therapy does not take place after the defibrillation pulse. Moreover, it would be desirable for IPD 16 to deliver post-shock pacing after delivery of a cardioversion/defibrillation pulse. Consequently, IPD 16 and ICD system 30a may be configured to coordinate their arrhythmia detection and treatment activities.

In some examples, IPD 16 and ICD system 30a may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages. Two-way communication and coordination of the delivery of patient therapies between IPD 16 and ICD system 30 is described in commonly-assigned U.S. Pat. No. 8,744,572 to Greenhut et al., titled, "SYSTEMS AND METHODS FOR LEADLESS PACING AND SHOCK THERAPY." and issued Jun. 3, 2014, the entire content of which is incorporated by reference herein.

However, device-to-device communication between ICD system 30 and IPD 16, but this may add complexity to the system and not be highly effective, e.g., not be fast enough in response time to prevent unwanted delivery of ATP after a defibrillation shock, or too slow to initiate post-shock pacing therapies at a preferred time post shock. In some examples described herein, IPD 16 may be configured to detect anti-tachyarrhythmia shocks delivered by ICD 9, which improve the coordination of therapy between subcutaneous ICD 9 and IPD 16 without requiring device-to-device communication.

IPD 16 may be configured to detect an anti-tachyarrhythmia shock delivered by ICD system 30 or an external defibrillator according to the detection of an electrical signal across two or more electrodes of IPD 16. IPD 16 may be configured to detect an anti-tachyarrhythmia shock based on electrical characteristics of the anti-tachyarrhythmia shock. Even though different defibrillation devices may provide different waveforms, including different pulse durations and amplitudes, defibrillation pulses generally have electrical signal characteristics such that detection of an anti-tachyarrhythmia shock can occur even without prior knowledge as to an anti-tachyarrhythmia shock waveform of an implanted or external defibrillator. In this manner, IPD 16 may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In some examples, IPD 16 detects the anti-tachyarrhythmia shock by measuring the voltage across the electrode inputs of the implanted device. IPD 16 may detect one or more signal characteristics of an anti-tachyarrhythmia shock including: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity. For example, IPD 16 may detect a high level of an anti-tachyarrhythmia shock in combination with one or both of the detection of a high slew rate of the leading and trailing edges, and the detection of a large post-shock polarization change. In general, IPD 16 may detect an anti-tachyarrhythmia shock by detecting an amplitude of a signal above a shock threshold. An amplitude of the signal may include an amplitude of a derivative of the signal.

In one example, IPD 16 may be configured to receive an indication of a detected cardiac arrhythmia eligible for anti-tachyarrhythmia shock therapy. IPD 16 may include a set of electrodes configured to be implanted within or near heart 26 of patient 14. In response to receiving the indication of the tachyarrhythmia, IPD 16 may enable shock detection circuitry of IPD 16 configured to detect delivery of anti-tachyarrhythmia shock therapy. The shock detection circuitry of IPD 16 may then detect delivery of anti-tachyarrhythmia shock therapy by measuring the voltage across the electrode inputs (e.g., detect that the shock has been delivered). The shock detection circuitry may apply one or more of the below-identified general techniques for detection of an anti-tachyarrhythmia shock that generally include detection of an amplitude of the signal above a shock threshold: detection of the high level of an anti-tachyarrhythmia shock, detection of a high slew rate of the leading and trailing edges, and detection of a large post-shock polarization change.

In response to detection of the anti-tachyarrhythmia shock, the IPD 16 may abort and/or temporarily suspend the delivery of ATP and to activate post-shock pacing, such as VVI (Ventricular sensing, Ventricular pacing, Inhibited pacing when activity sensed) post-shock pacing. ATP may remain suspended temporarily following an anti-tachyarrhythmia shock to ensure that the relatively higher-rate pacing pulses will not induce another arrhythmia. Additionally, post-shock pacing may be used to ensure pacing support if the patient's heart does not begin to beat normally immediately following an anti-tachyarrhythmia shock.

IPD 16 may deliver post-shock pacing according to a post-shock pacing mode. The post-shock pacing mode may specify a higher than normal pacing pulse magnitude (relative to typical cardiac pacing), e.g., higher than normal pulse amplitude and/or pulse width, to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during ventricular fibrillation (VF). Furthermore, after an anti-tachyarrhythmia shock there can be increased polarization at the lead interface resulting in the need for a higher magnitude to overcome the lead polarization. In some examples, the post-shock pacing mode may specify a value for a timer, used by IPD 16 to control how long post-shock pacing is delivered after delivery of the shock.

In some examples, in addition to being configured to detect the shock in the sensed electrical signal, IPD 16 may be configured to determine that another medical device. e.g., ICD system 30a, delivered a shock based on detecting asystole. IPD 16 may detect asystole based on the sensed electrical signal, e.g., based on not detecting a depolarization of heart 26 within an asystole threshold period of time. IPD 16 may compare the asystole threshold to a period of time beginning upon a most recent depolarization of heart 26, detection of a tachyarrhythmia, or termination of delivery of ATP by IPD 16, as examples.

In some examples IPD 16 detects a tachyarrhythmia based on the electrical signal sensed via at least a subset of its electrodes, and begins shock detection and asystole detection in response to detecting the tachyarrhythmia. In some examples, IPD 16 delivers ATP in response to detection the tachyarrhythmia, and begins shock detection and asystole detection in response to end the delivery of ATP. In some examples, IPD 16 determines that a shock was delivered by another medical device based on detecting asystole within a threshold period of time following detection of a tachyarrhythmia. Being configured to both detect a shock, and determine that a shock was delivered based on asystole, may allow IPD 16 to provide post-shock pacing in situations in which IPD 16 and extracardiovascular ICD system 30a do not communicate, and IPD 16 is unable to reliably detect delivery of a shock by ICD system 30a.

IPD 16 may also re-start post-shock pacing if IPD 16 determines that additional shocks have been delivered. For example, IPD 16 may be configured to begin delivery of post-shock pacing after delivery of a first shock. IPD 16 may subsequently identify delivery of a second shock, and, in response to the detection of the second shock, re-start delivery of the post-shock pacing if needed. IPD 16 may continue to re-start post-shock pacing as long as additional shocks are delivered.

In some examples, IPD 16 may terminate post-shock pacing in response to various indicators. For example, IPD 16 may track a period of time following the start of post-shock pacing. IPD 16 may then determine that the period of time exceeds a timeout threshold. For example, IPD 16 may use a timer to track this period of time. In response to the determination, IPD 16 may terminate delivery of post-shock pacing. In other examples, IPD 16 may terminate post-shock pacing after delivery of a predetermined number of pacing pulses. Alternatively, IPD 16 may terminate post-shock pacing in response to detection of a normal sinus rhythm or receiving a communication from ICD system 30 instructing IPD 16 to terminate post-shock pacing.

After terminating post-shock pacing according to a post-shock pacing mode, IPD 16 may revert to a baseline pacing mode, such as bradycardia pacing. To revert to the baseline pacing mode, IPD 16 may iteratively test a plurality of decreasing values of pacing pulse magnitude until loss of capture is detected. IPD 16 may update a baseline pacing pulse magnitude for the baseline pacing mode based on the loss of capture, e.g., based on a pacing pulse magnitude immediately prior to the pacing pulse magnitude that failed to capture heart 26 according to the decreasing progression of pacing pulse magnitudes.

External device 21 may be configured to communicate with one or both of ICD system 30a and IPD 16. In examples where external device 21 only communicates with one of ICD system 30a and IPD 16, the non-communicative device may receive instructions from or transmit data to the device in communication with device 21. In some examples, external device 21 comprises a handheld computing device, computer workstation, or networked computing device. External device 21 may include a user interface that receives input from a user. In other examples, the user may also interact with device 21 remotely via a networked computing device. The user may interact with external device 21 to communicate with IPD 16 and/or ICD system 30.

For example, the user may interact with external device 21 to send an interrogation request and retrieve sensed physiological data or therapy delivery data stored by one or both of IPD 16 and ICD system 30a, and program or update therapy parameters that define therapy, or perform any other activities with respect to IPD 16 and/or ICD system 30a. Although the user is a physician, technician, surgeon, electrophysiologist, or other healthcare professional, the user may be patient 14 in some examples. For example, external device 21 may allow a user to program any thresholds, e.g., amplitudes or interval, or other data described herein as being used by IPD 16 to detect tachyarrhythmias, shocks and/or asystole, and may program any parameters described herein that control the delivery of pacing, including baseline (e.g., bradycardia) pacing and post-shock pacing by IPD 16.

External device 21 may communicate with IPD 16 and/or ICD system 30a via wireless communication using any techniques known in the art. Examples of communication techniques may include, for example, proprietary and non-proprietary radiofrequency (RF) telemetry, but other techniques are also contemplated. In some examples, external device 21 may include a programming head that may be placed proximate to the patient's body near the IPD 16 and/or ICD system 30a implant site in order to improve the quality or security of communication between IPD 16 and/or ICD system 30a and device 21.

Although FIGS. 1A-1C are shown or described in the context of IPD 16 and extracardiovascular ICD system 30a that includes lead 12a with a substernally placed distal portion, techniques in accordance with one or more aspects of the present disclosure may be applicable to other coexistent systems. For example, an extracardiovascular ICD system may include a lead having a distal portion that is implanted subcutaneously above the sternum (or other location) instead of being implanted substernally. As another example, instead of an IPD, a pacing system may be implanted having a pacemaker and one or more leads connected to and extending from the pacemaker into one or more chambers of the heart or attached to the outside of the heart to provide pacing therapy to the one or more chambers. As such, the example of FIGS. 1A-1C is illustrated for example purposes only and should not be considered limiting of the techniques described herein.

Figure 2:
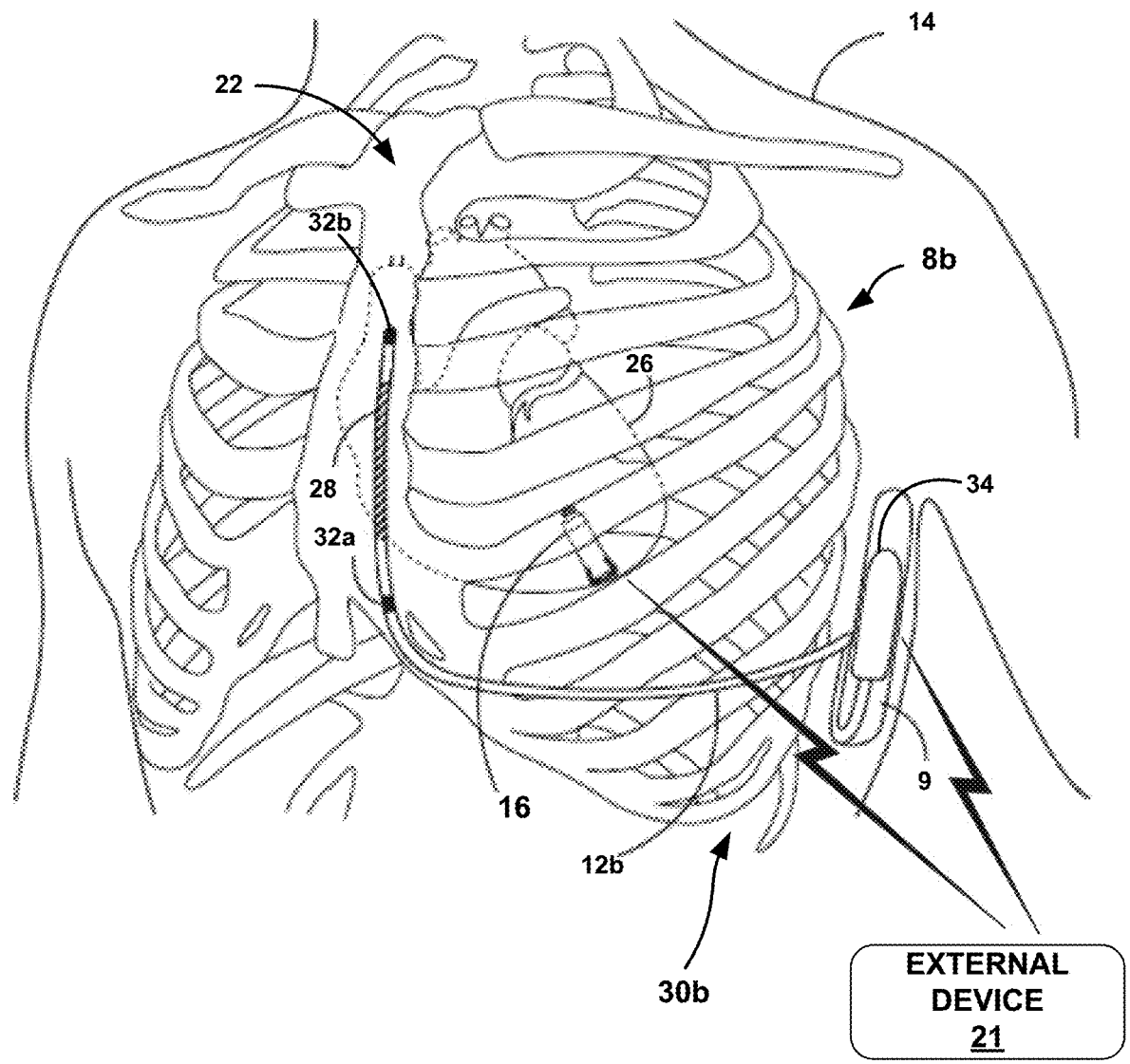
FIG. 2 is a front view of another example medical device system that includes an extracardiovascular ICD system and an IPD implanted within a patient.

FIG. 2 is a front view of another example medical device system 8b that includes an extracardiovascular ICD system 30b and IPD 16 implanted within a patient. Medical device system 8b may be configured to perform any of the techniques described herein with respect to medical device system 8a of FIGS. 1A-1C. For example, IPD 16 may be both configured to detect shocks delivered by extracardiovascular ICD system 30b in a sensed electrical signal, and determine whether a shock was delivered by extracardiovascular ICD system 30b based on detecting asystole. IPD 16 may also be configured to revert from a post-shock pacing mode to a baseline pacing mode, as described herein. Components with like numbers in FIGS. 1A-1C and FIG. 2 may be similarly configured and provide similar functionality.

In the example of FIG. 2, extracardiovascular ICD system 30b includes ICD 9 coupled to a defibrillation lead 12b. Unlike defibrillation lead 12a of FIGS. 1A-1C, defibrillation lead 12b extends subcutaneously above the ribcage from ICD 9. In the illustrated example, defibrillation lead 12b extends toward a center of the torso of patient 14, bends or turns near the center of the torso, and extends subcutaneously superior above the ribcage and/or sternum 22. Defibrillation lead 12b may be offset laterally to the left or the right of sternum 22 or located over sternum 22. Defibrillation lead 12b may extend substantially parallel to sternum 22 or be angled lateral from the sternum at either the proximal or distal end.

Defibrillation lead 12b includes an insulative lead body having a proximal end that includes a connector 34 configured to be connected to ICD 9 and a distal portion that includes one or more electrodes. Defibrillation lead 12b also includes one or more conductors that form an electrically conductive path within the lead body and interconnect the electrical connector and respective ones of the electrodes. In the illustrated example, defibrillation lead 12b includes a single defibrillation electrode 28 toward the distal portion of defibrillation lead 12b, e.g., toward the portion of defibrillation lead 12b extending along sternum 22. Defibrillation lead 12b is placed along sternum such that a therapy vector between defibrillation electrode 28 and a housing electrode formed by or on ICD 9 (or other second electrode of the therapy vector) is substantially across a ventricle of heart 26.

Defibrillation lead 12b may also include one or more sensing electrodes, such as sensing electrodes 32a and 32b, located along the distal portion of defibrillation lead 12b. In the example illustrated in FIG. 2, sensing electrodes 32a and 32b are separated from one another by defibrillation electrode 28. In other examples, however, sensing electrodes 32a and 32b may be both distal of defibrillation electrode 28 or both proximal of defibrillation electrode 28. In other examples, lead 12b may include more or fewer electrodes at various locations proximal and/or distal to defibrillation electrode 28, and lead 12b may include multiple defibrillation electrodes, e.g., defibrillation electrodes 28a and 28b as illustrated in the example of FIGS. 1A-1C. IPD 16 may be configured to detect shocks delivered by ICD 9 via lead 12b, or determine that shocks were delivered based on detect asystole.

Figure 3:
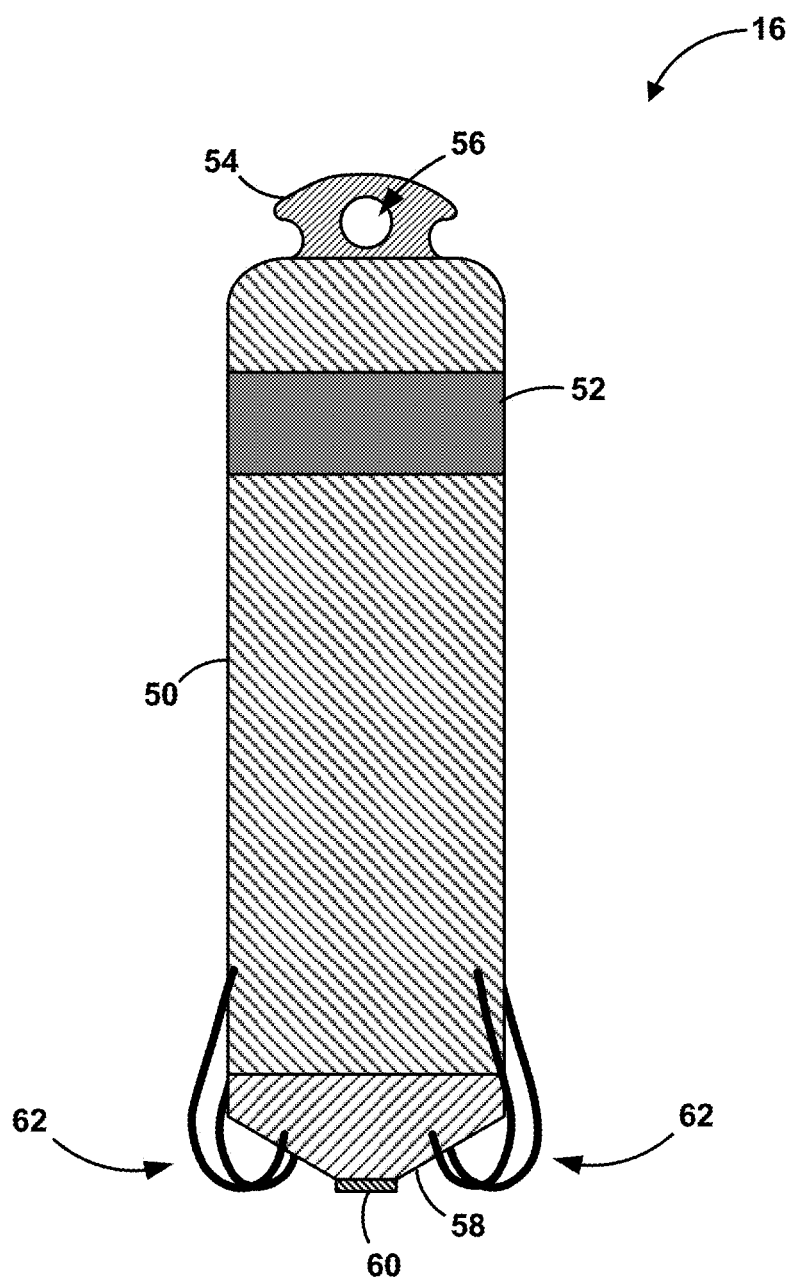
FIG. 3 is a conceptual drawing illustrating an example configuration of the IPD of FIGS. 1A-1C and 2.

FIG. 3 is a conceptual drawing illustrating an example configuration of IPD 16 that may utilize the shock detection and asystole detection techniques of this disclosure, as well as the post-shock pacing mode reversion techniques of this disclosure. As shown in FIG. 3, IPD 16 includes case 50, cap 58, electrode 60, electrode 52, fixation mechanisms 62, flange 54, and opening 56. Together, case 50 and cap 58 may be considered the housing of IPD 16. In this manner, case 50 and cap 58 may enclose and protect the various electrical components within IPD 16. Case 50 may enclose substantially all of the electrical components, and cap 58 may seal case 50 and create the hermetically sealed housing of IPD 16. Although IPD 16 is generally described as including one or more electrodes, IPD 16 may typically include at least two electrodes (e.g., electrodes 52 and 60) to deliver an electrical signal (e.g., therapy such as ATP) and/or provide at least one sensing vector.

Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating.

Electrode 60 may be used as a cathode and electrode 52 may be used as an anode, or vice versa, for delivering cardiac pacing such as bradycardia pacing, ATP, or post-shock pacing. However, electrodes 52 and 60 may be used in any stimulation configuration. In addition, electrodes 52 and 60 may be used to detect intrinsic electrical signals from cardiac muscle as well as asystole (i.e., the absence of cardiac depolarizations) and shocks delivered by another medical device, e.g., ICD systems 30a and 30b of FIGS. 1A-2. Cardiac pacing delivered by IPD 16, as compared with alternative devices, may be considered to be "painless" to patient 14 or even undetectable by patient 14 since the electrical stimulation occurs very close to or at cardiac muscle and at relatively low energy levels.

Fixation mechanisms 62 may attach IPD 16 to cardiac tissue. Fixation mechanisms 62 may be active fixation tines, screws, clamps, adhesive members, or any other mechanisms for attaching a device to tissue. As shown in the example of FIG. 3, fixation mechanisms 62 may be constructed of a memory material, such as a shape memory alloy (e.g., nickel titanium), that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of IPD 16. For example, a suture or other device may be inserted around flange 54 and/or through opening 56 and attached to tissue. In this manner, flange 54 may provide a secondary attachment structure to tether or retain IPD 16 within heart 26 if fixation mechanisms 62 fail. Flange 54 and/or opening 56 may also be used to extract IPD 16 once the IPD needs to be explanted (or removed) from patient 14 if such action is deemed necessary.

The techniques described herein are generally described with regard to a leadless pacing device or intracardiac pacing device such as IPD 16. IPD 16 may be an example of a pacing device configured to implement the techniques of this disclosure. However, other implantable medical devices may be used to perform the same or similar functions as IPD 16, e.g., determining whether another device delivered an anti-tachyarrhythmia shock and reverting from a post-shock pacing mode to a baseline pacing mode.

For example, an IPD may include a small housing that carries an electrode, similar to IPD 16, and configured to be implanted within a chamber of heart 26. The IPD may also include one or more relatively short leads configured to place one or more respective additional electrodes at another location within the same chamber of the heart or a different chamber of the heart. In this manner, the housing of the IPD may not carry all of the electrodes used to perform functions described herein with respect to IPD 16. In other examples, each electrode of the IPD may be carried by one or more leads (e.g., the housing of the IPD may not carry any of the electrodes). In some examples, an IPD or other pacing device may include or be coupled to three or more electrodes, where each electrode may deliver therapy and/or detect intrinsic signals.

In another example, a pacing device may be configured to be implanted external to heart 26, e.g., near or attached to the epicardium of heart 26. An electrode carried by the housing of the pacing may be placed in contact with the epicardium and/or one or more electrodes of leads coupled to the pacing may be placed in contact with the epicardium at locations sufficient to provide cardiac pacing. In still other examples, a pacing device configured to perform the techniques described herein may be implanted subcutaneously or submuscularly, and connected to one or more intracardiac leads carrying one or more electrodes.

Figure 4:
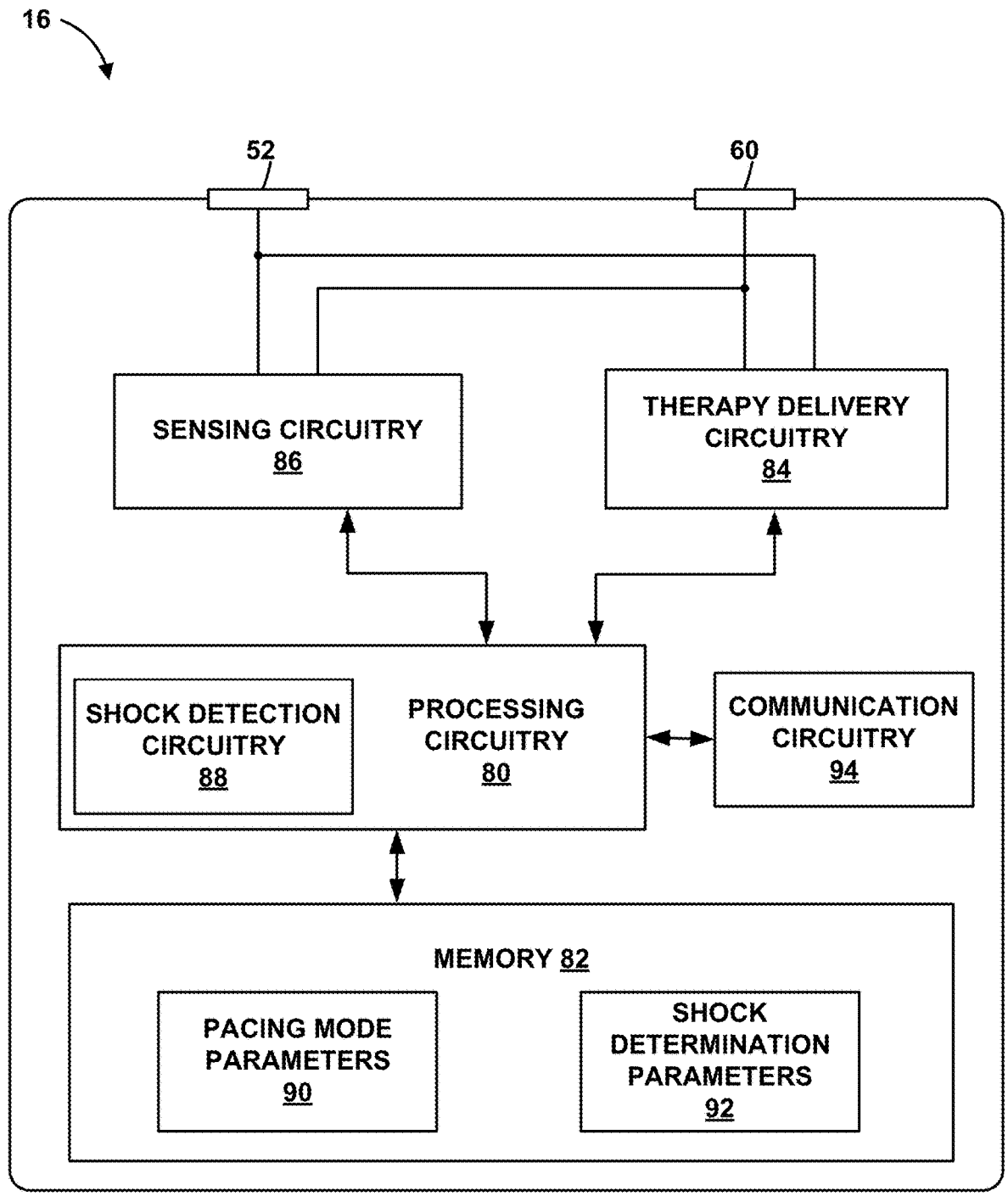
FIG. 4 is a functional block diagram illustrating an example configuration of the IPD of FIGS. 1A-1C and 2.

FIG. 4 is a functional block diagram illustrating an example configuration of IPD 16. In the illustrated example, IPD 16 includes a processing circuitry 80 and an associated memory 82, therapy delivery circuitry 84, sensing circuitry 86, shock detection circuitry 88, and communication circuitry 94. Memory 82 includes computer-readable instructions that, when executed by processing circuitry 80, cause IPD 16 and processing circuitry 80 to perform various functions attributed to IPD 16 and processing circuitry 80 herein (e.g., delivering baseline pacing, detecting arrhythmias, delivering ATP, determining that another device delivered a shock, delivering post-shock pacing, and reverting from post-shock pacing to baseline pacing). Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 80 may include fixed function circuitry and/or programmable processing circuitry. Processing circuitry 80 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 80 may include multiple components, such as any combination of one or more microprocessors, one or more controllers, one or more DSPs, one or more ASICs, or one or more FPGAs, as well as other discrete or integrated logic circuitry. The functions attributed to processing circuitry 80 herein may be embodied as software, firmware, hardware or any combination thereof.

Processing circuitry 80 controls therapy delivery circuitry 84 to deliver cardiac pacing pulses to heart 26 according to therapy parameters, including pacing mode parameters 90, which may be stored in memory 82. For example, processing circuitry 80 may control therapy delivery circuitry 84 to deliver electrical pulses with the magnitudes (e.g., amplitudes and pulse widths), frequency, and polarities of electrodes 52 and 60 specified by the therapy parameters. In the illustrated example, therapy delivery circuitry 84 is electrically coupled to electrodes 52 and 60 carried on the housing of IPD 16.

Pacing mode parameters 90 include parameters that define how IPD 16 delivers cardiac pacing according a plurality of pacing modes, e.g., as controlled by processing circuitry 80. The pacing modes may include a baseline pacing mode, which may be bradycardia pacing, an ATP mode, and a post-shock pacing mode. Pacing mode parameters 90 may also define how IPD 16 reverts from the post-shock pacing mode to the baseline pacing mode.

ATP pacing mode parameters may include a pulse interval defined based on a fraction of a detected ventricular tachycardia (VT) cycle length. The interval may be between approximately 150 milliseconds and 500 milliseconds (e.g., between approximately 2.0 hertz and 7.0 hertz), and a pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate. In addition, trains of pulses in successive ATP periods may be delivered at increasing pulse rate in an attempt to capture the heart and terminate the tachycardia. Example ATP parameters and other criteria involving the delivery of ATP are described in U.S. Pat. No. 6,892,094 to Ousdigian et al., entitled, "COMBINED ANTI-TACHYCARDIA PACING (ATP) AND HIGH VOLTAGE THERAPY FOR TREATING VENTRICULAR ARRHYTHMIAS," and issued on May 10, 2005, the entire content of which is incorporated herein by reference.

Pacing mode parameters 90 may also define parameters for a post-shock pacing mode, such as a post-shock value of pacing pulse magnitude. In one example, monophasic post-shock pacing therapy may have a pulse width of approximately 1 millisecond at each phase and a pulse amplitude of approximately 5 volts. The pacing rate may be set to 30-60 beats per minute (0.5-1 hertz). The duration of each post-shock pacing session may be between 10 seconds and 60 seconds, or even longer in other examples. Pacing mode parameters 90 for the post-shock pacing mode may include an interval or period that defines the duration of each post-shock pacing session. The post-shock value of pacing pulse magnitude may be set to the greatest pacing pulse magnitude value at which IPD 16 is configurable to deliver pacing pulses.

Pacing mode parameters 90 may also define parameters for a baseline pacing mode, such as bradycardia pacing, including a baseline value of the pacing pulse magnitude, e.g., pulse amplitude and/or pulse width. Processing circuitry 80 may perform capture management to determine the baseline value of pacing pulse magnitude. For example, processing circuitry 80 may determine whether pacing pulses delivered according to the baseline pacing mode captured heart 26 and, if loss of capture is detected, increase the pacing pulse magnitude until the heart is captured. Processing circuitry 80 may periodically control therapy delivery circuitry 84 to deliver one or more pacing pulses having a magnitude below the baseline value, and determine whether the lower magnitude pacing pulse captured heart 26. If the lower magnitude pacing pulse(s) capture heart 26, processing circuitry 80 may accordingly lower the baseline value of pacing pulse magnitude. The pacing mode parameters 90 for the baseline pacing mode may also include parameters that control the timing of pacing pulse delivery relative to a sensed cardiac depolarization.

Therapy delivery circuitry 84 may include charging circuitry, one or more charge storage devices, such as one or more capacitors, and switching circuitry that controls when the capacitor(s) are discharged to electrodes 52 and 60 and the width of pacing pulses. Charging of capacitors to a programmed pacing pulse amplitude and discharging of the capacitors for a programmed pulse width may be performed by therapy delivery circuitry 84 according to control signals received from processing circuitry 80, which are provided by processing circuitry 80 according to pacing mode parameters 90 stored in memory 82.

Electrical sensing circuitry 86 monitors signals from electrodes 52 and 60 in order to monitor electrical activity of heart 26, impedance, or other electrical phenomenon. Sensing may be done to determine heart rates or heart rate variability, or to detect arrhythmias (e.g., tachyarrhythmias or bradycardia) or other electrical signals. In some examples, sensing circuitry 86 may include one or more filters and amplifiers for filtering and amplifying a signal received from electrodes 52 and 60. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 86 outputs an indication to processing circuitry 80 in response to sensing of a cardiac event (e.g., detected P-waves or R-waves). In this manner, processing circuitry 80 may receive detected cardiac event signals corresponding to the occurrence of detected R-waves and P-waves in the respective chambers of heart 26. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 86 may also include a switch module to select which of the available electrodes (or electrode polarities) are used to sense the heart activity. In examples with several electrodes, processing circuitry 80 may select the electrodes that function as sense electrodes, i.e., select the sensing configuration, via the switch module within sensing circuitry 86. Sensing circuitry 86 may also pass one or more digitized EGM signals to processing circuitry 80 for analysis, e.g., for use in cardiac rhythm discrimination.

Processing circuitry 80 may implement programmable counters. If IPD 16 is configured to generate and deliver pacing pulses to heart 26, such counters may control the basic time intervals associated with bradycardia pacing (e.g., DDD, VVI, DVI, VDD, AAI, DDI, DDDR, VVIR, DVIR, VDDR, AAIR, DDIR pacing) and other modes of pacing. Intervals defined by processing circuitry 80 may include atrial and ventricular pacing escape intervals, refractory periods during which sensed P-waves and R-waves are ineffective to restart timing of the escape intervals, and the pulse widths of the pacing pulses. The durations of these intervals may be determined by processing circuitry 80 in response to pacing mode parameters 90 in memory 82.

Interval counters implemented by processing circuitry 80 may be reset upon sensing of R-waves and P-waves with detection channels of sensing circuitry 86. In examples in which IPD 16 provides pacing, therapy delivery circuitry 84 may include pacer output circuits that are coupled to electrodes 52 and 60, for example, and are appropriate for delivery of a bipolar or unipolar pacing pulse to one of the chambers of heart 26. In such examples, processing circuitry 80 may reset the interval counters upon the generation of pacing pulses by therapy delivery circuitry 84, and thereby control the basic timing of cardiac pacing functions, including baseline or bradycardia pacing, ATP, or post-shock pacing.

The value of the count present in the interval counters when reset by sensed R-waves and P-waves may be used by processing circuitry 80 to measure the durations of R-R intervals, P-P intervals, P-R intervals and R-P intervals, which are measurements that may be stored in memory 82. Processing circuitry 80 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 82 may be configured as a plurality of recirculating buffers, capable of holding series of measured intervals, which may be analyzed by processing circuitry 80 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS." which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS." which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 80 in other examples.

In some examples, processing circuitry 80 may determine that tachyarrhythmia has occurred by identification of shortened R-R (or P-P) interval lengths. Generally, processing circuitry 80 detects tachycardia when the interval length falls below 220 milliseconds and fibrillation when the interval length falls below 180 milliseconds. In other examples, processing circuitry 80 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples. In other examples, additional physiological parameters may be used to detect an arrhythmia. For example, processing circuitry 80 may analyze one or more morphology measurements, impedances, or any other physiological measurements to determine that patient 14 is experiencing a tachyarrhythmia.

In addition to detecting and identifying specific types of cardiac events, e.g., cardiac depolarizations, sensing circuitry 86 may also sample the detected intrinsic signals to generate an electrogram or other time-based indication of cardiac events. Sensing circuitry 86 may include an analogto-digital converter or other circuitry configured to sample and digitize the electrical signal sensed via electrodes 52 and 60. Processing circuitry 80 may analyze the digitized signal for a variety of purposes, including morphological identification or confirmation of tachyarrhythmia of heart 26, and detection of evoked responses to pacing pulses to determine whether the pacing pulses captured heart 26.

Processing circuitry 80 may also analyze the digitized signal to detect delivery of an anti-tachyarrhythmia shock by another medical device, e.g., extracardiovascular ICD system 30a or 30b. In the example of FIG. 4, processing circuitry 80 includes shock detection circuitry 88 configured to analyze the digitized signal to detect delivery of an anti-tachyarrhythmia shock by another medical device. In some examples, the shock detection functionality attributed to shock detection circuitry 88 may be a functional module executed by processing circuitry 80.

Shock detection circuitry 88 may be used to detect anti-tachyarrhythmia shocks delivered by ICD system 30a or 30b, or another device. For example, processing circuitry 80 may enable shock detection circuitry 88 in response to detecting a tachyarrhythmia or receiving a communication indicating that an arrhythmia has been detected or a shock is imminent. Processing circuitry 80 may also disable shock detection circuitry 88 after a predetermined time period has elapsed or when a shock is otherwise not (or no longer) anticipated. When shock detection circuitry 88 is enabled, shock detection circuitry 88 may identify when an electrical signal received by sensing circuitry 86 is representative of a cardioversion or defibrillation pulse.

In response to detecting a shock via shock detection circuitry 88, processing circuitry 80 may begin post-shock pacing according to a post-shock pacing mode when such functionality has been enabled for therapy. Processing circuitry 80 may also re-start post-shock pacing in response to detecting additional shocks via shock detection circuitry 88. In some examples, processing circuitry 80 may terminate ATP upon detection of a shock.

Shock detection circuitry 88 may detect an anti-tachyarrhythmia shock, e.g., a defibrillation or cardioversion pulse, delivered by ICD systems 30a or 30b, or an external defibrillator, based on the detection of an electrical signal across two or more electrodes, such as electrodes 52 and 60. In order to detect the anti-tachyarrhythmia shock, shock detection circuitry 88 may detect one or more signal characteristics of an anti-tachyarrhythmia shock in the signal including: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity of the shock anti-tachyarrhythmia shock detection.

In general, IPD 16 may detect an anti-tachyarrhythmia shock by detecting an amplitude of the digitized version of the electrical signal sensed by sensing circuitry 86 that is above a shock threshold. An amplitude above the shock threshold may reflect, for example, a high amplitude level of the electrical signal and/or polarization across electrodes associated with delivery of an anti-tachyarrhythmia shock by another medical device. An amplitude of the signal may include an amplitude of a derivative of the signal, and a high derivative amplitude may indicate the high slew rate of the leading and trailing edges of the shock waveform. In some examples, IPD 16 (e.g., shock detection circuitry 88 and/or processing circuitry 80) may implement any of the anti-tachyarrhythmia shock detection techniques described in commonly-assigned U.S. Pat. No. 9,278,229 to Reinke et al., titled, "ANTI-TACHYARRHYTHMIA SHOCK DETECTION," and issued Mar. 8, 2016, the entire content of which is incorporated by reference herein. One or more shock thresholds or other shock detection parameters 92 used by shock detection circuitry 88 and processing circuitry 80 to detect shocks may be stored in memory 92.

Processing circuitry 80 is also configured to detect asystole of heart 26. Processing circuitry 80 is configured to determine, without detecting the delivery of the anti-tachyarrhythmia shock, that the other medical device, e.g., extracardiovascular ICD systems 30a or 30b, delivered the anti-tachyarrhythmia shock based on the detection of asystole. Asystole of heart 26 may result from delivery of the anti-tachyarrhythmia shock and, accordingly, detection of asystole may indicate the other device has delivered the anti-tachyarrhythmia shock.

Processing circuitry 80 may detect asystole based on an absence of a cardiac depolarization, e.g., the absence of an indication of a cardiac depolarization from sensing circuitry 86, for at least a threshold period of time, which may be referred to as an asystole threshold, and stored as part of shock detection parameters 92 in memory 82. The asystole threshold may be between 1 and 10 seconds, such as 2 to 5 seconds, as examples. Processing circuitry 80 may compare the asystole threshold to a period of time beginning upon a most recent depolarization of heart 26, detection of a tachyarrhythmia, or termination of delivery of ATP by IPD 16, as examples, and the asystole threshold may vary depending on which event triggered initiation of the time period to which the threshold will be compared.

In some examples, processing circuitry 80 detects a tachyarrhythmia, e.g., as described above, and, in response to detecting the tachyarrhythmia, starts a timer to compare to the asystole threshold and controls shock detection circuitry 88 to begin shock detection. In some examples in which processing circuitry 80 controls therapy delivery circuitry 84 to deliver ATP in response to detecting the tachyarrhythmia, processing circuitry 80 initiates the shock detection and asystole detection in response to end the delivery of ATP. In either of these examples, processing circuitry 80 determines that a shock was delivered by another medical device based on detecting asystole within a threshold period of time following detection of a tachyarrhythmia. In examples in which IPD 16 does not detect a tachyarrhythmia and delivers bradycardia pacing, processing circuitry 80 may control therapy delivery circuitry 84 to suspend bradycardia pacing for one or more cardiac cycles to facilitate detection of prolonged asystole.

In response to determining that another medical device delivered an anti-tachyarrhythmia shock, processing circuitry 80 controls therapy delivery circuitry 84 to deliver post-shock pacing via electrodes 52 and 60 according to a post-shock pacing mode stored in pacing mode parameters 90 within memory 82. Pacing mode parameters 90 stored in memory 82 may include a baseline value of a pacing pulse magnitude for delivery of pacing pulses according to a baseline pacing mode, e.g., bradycardia pacing, and a post-shock value of the pacing pulse magnitude for delivery of pacing pulses according to a post-shock pacing mode. The post-shock value of the pacing pulse magnitude is greater than the baseline value. Again, pacing pulse magnitude may include one or both of pacing pulse amplitude and pacing pulse width. Pacing mode parameters 90 for the post-shock pacing mode may also include a length of time and/or number of pulses for delivery of post-shock pacing according to the post-shock pacing mode.

Processing circuitry 80 may also revert IPD 16 from the post-shock pacing mode to the baseline pacing mode, e.g., after the length of time or number of pulses. For the reversion, processing circuitry 80 may control therapy delivery circuitry 84 to deliver a plurality of pacing pulses to heart 26 via electrodes 52 and 60. The values of the pacing pulse magnitude for the plurality of pacing pulses are configured to perform a downward capture threshold test by iteratively testing a plurality of values a pacing pulse magnitude that decrease from an initial reversion value, which may be greater than the baseline value and less than the post-shock value. The initial reversion value may be stored as part of pacing mode parameters 90 in memory 82. Processing circuitry 80 may control therapy delivery circuitry 84 to test decreasing values of the pacing pulse magnitude until loss of capture is detected. To determine whether the pacing pulses captured heart 26, processing circuitry 80 may, based on the electrical signal sensed by sensing circuitry 86 via electrodes 52 and 60, determine whether an evoked response of heart 26 was caused by the pacing pulses, e.g., by each of the pacing pulses.

During the iterative testing of decreasing pacing pulse magnitude values, processing circuitry 80 may control therapy delivery circuitry 84 to increase the rate at which pacing pulses are delivered, thereby suppressing intrinsic depolarizations, and ensuring that detected cardiac activity is in response to the pacing pulses. In some examples, processing circuitry 80 controls therapy delivery circuitry to decrease the pacing pulse magnitude every cardiac cycle, or every N cardiac cycles. The frequency and size of pacing pulse magnitude reductions during reversion may be stored as pacing mode parameters 90 in memory 82.

In other examples of iteratively testing decreasing magnitude values, one or more test pacing pulses at a next, lower test value of pacing pulse magnitude are preceded and/or followed, in one or more preceding or subsequent cardiac cycles, by one or more support pulses at the current value of pacing pulse magnitude. If the test pacing pulses capture heart 26, the successful test value becomes the current value, and another lower, test value of pacing pulse magnitude may be similarly tested. If a test pacing pulse fails to capture heart 26, processing circuitry 80 may control therapy deliver circuitry 84 to deliver, within the same cardiac cycle, a back-up pacing pulse with at least the current value of pacing pulse magnitude, to ensure that heart 26 is paced. In the event that a test pacing pulse failed to capture heart 26, processing circuitry 80 may control therapy delivery circuitry to re-attempt one or more test pacing pulses at the test value of pacing pulse magnitude, or end the iterative testing of decreasing magnitude values with a determination that the test value failed to capture heart 26.

Based on the detection of loss of capture of one of the plurality of values of pacing pulse magnitude, processing circuitry 80 may update the baseline value of the pacing pulse magnitude for the baseline pacing mode stored as one of pacing mode parameters 90 in memory 82. For example, processing circuitry 80 may determine the pacing pulse magnitude that preceded the one of the plurality of pacing pulses that failed to capture the heart, and update the baseline value based on the determined value of the pacing pulse magnitude. For example, processing circuitry 80 may update the baseline value to be a predetermined or programmable margin above the magnitude that preceded loss of capture of heart 26. Processing circuitry 80 may control therapy delivery circuitry 84 to deliver pacing pulse having the updated baseline value of magnitude according to the baseline pacing mode, e.g., a bradycardia pacing mode.

In some examples, in response to determining that the initial reversion value of the pacing pulse magnitude failed to capture the heart, processing circuitry 80 may suspend the reversion to the baseline pacing mode. The failure of the initial reversion magnitude pacing pulse to capture heart 26 may indicate that heart 26 is not ready for pacing according to the baseline pacing mode and/or would benefit from further pacing according to the post-shock pacing mode. Processing circuitry 80 may control therapy delivery circuitry 84 to stop iterative testing of decreasing magnitudes, and then deliver one or more pacing pulses having the post-shock value of the pacing magnitude. The return to post-shock pacing may be for a period of time or number of pulses, which may be stored as a pacing mode parameter 90 in memory 82. Processing circuitry 80 may then restart the reversion, e.g., by controlling therapy delivery circuitry 84 to deliver pacing pulses configured to iterative test the decreasing magnitudes.

Communication circuitry 94 includes any suitable hardware, firmware, software or any combination thereof for communicating with another device, such as external device 21 or ICD system 30a or 30b. Under the control of processing circuitry 80, communication circuitry 94 may receive downlink telemetry from and send uplink telemetry to external device 21 with the aid of an antenna, which may be internal and/or external. Processing circuitry 80 may provide the data to be uplinked to device 21 and the control signals for the telemetry circuitry within communication circuitry 94. e.g., via an address/data bus. In some examples, communication circuitry 94 may provide received data to processing circuitry 80 via a multiplexer. In some examples, communication circuitry 94 may communicate with a local external device, and processing circuitry 80 may communicate with a networked computing device via the local external device and a computer network, such as the Medtronic CareLink® Network developed by Medtronic, plc, of Dublin, Ireland.

A clinician or other user may retrieve data from IPD 16 using external device 21 or another local or networked computing device configured to communicate with processing circuitry 80 via communication circuitry 94. The clinician may also program parameters of IPD 16 using external device 21 or another local or networked computing device. In some examples, the clinician may program any of the magnitude values, thresholds, time periods, number of pulses, or other parameters discussed herein, such as those stored in memory as pacing mode parameters 90 and shock determination parameters 92.

Figure 5:
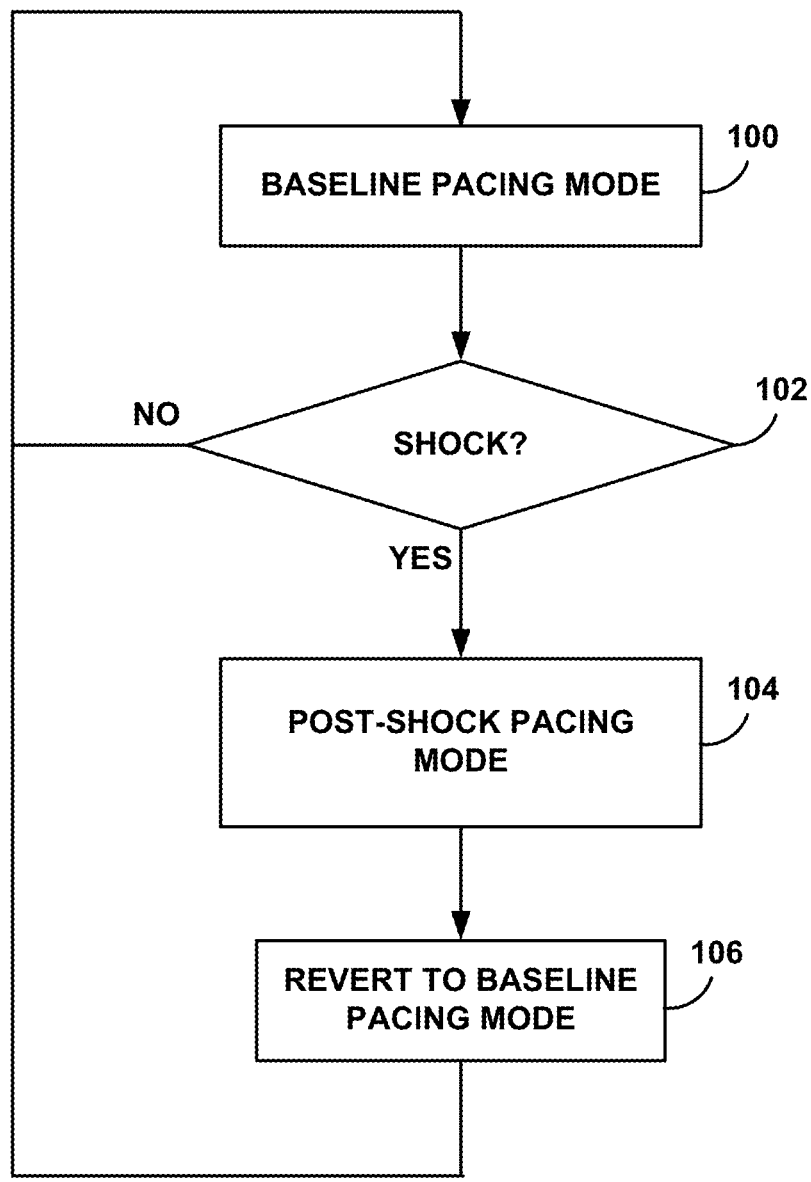
FIG. 5 is a flow diagram illustrating an example technique for transitioning from a baseline pacing mode to a post-shock pacing mode in response to determining that an anti-tachyarrhythmia shock was delivered, and reverting from the post-shock pacing mode to the baseline pacing mode.
Figure 6:
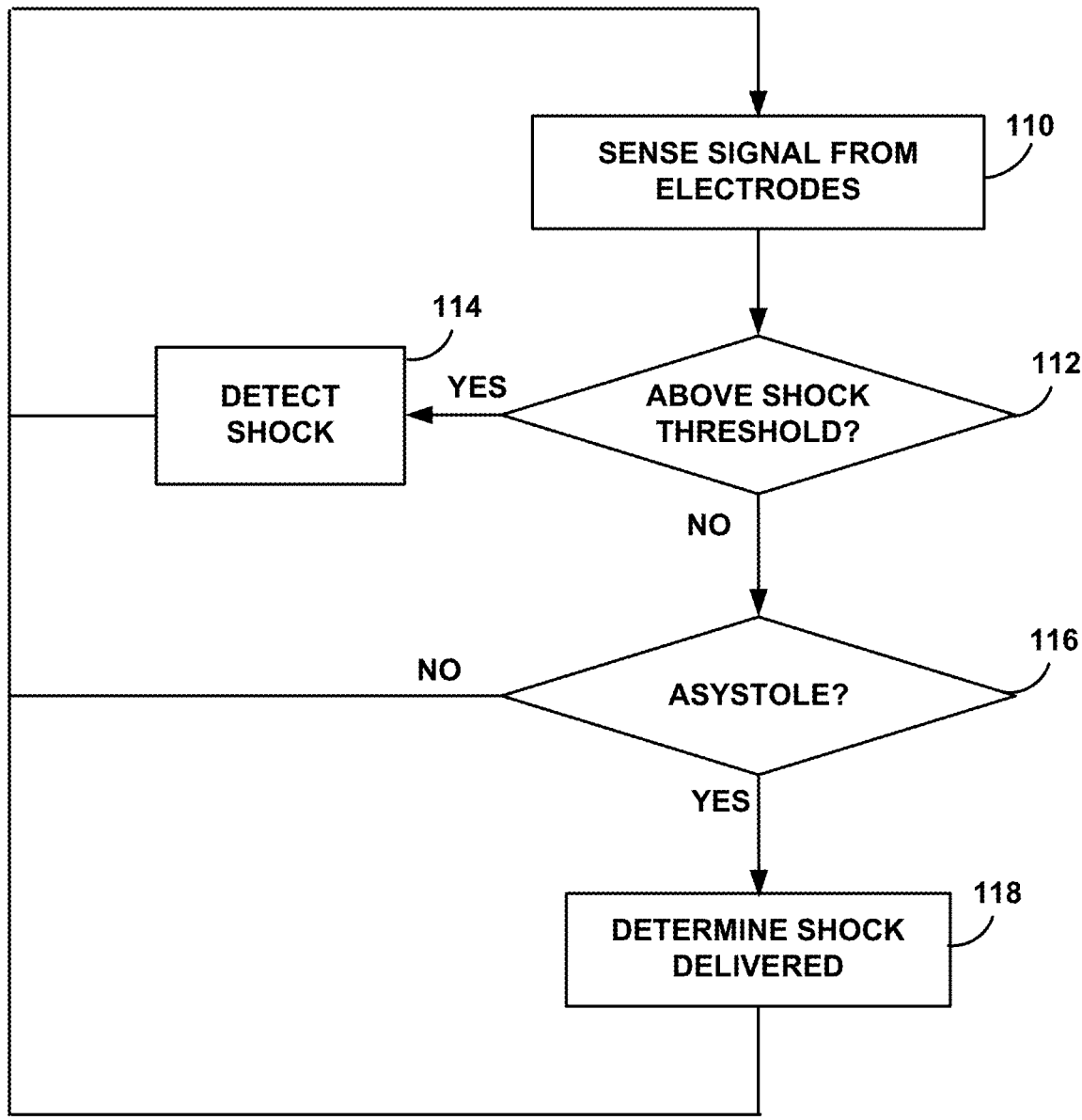
FIG. 6 is a flow diagram illustrating an example technique for determining whether an anti-tachyarrhythmia shock was delivered.
Figure 7:
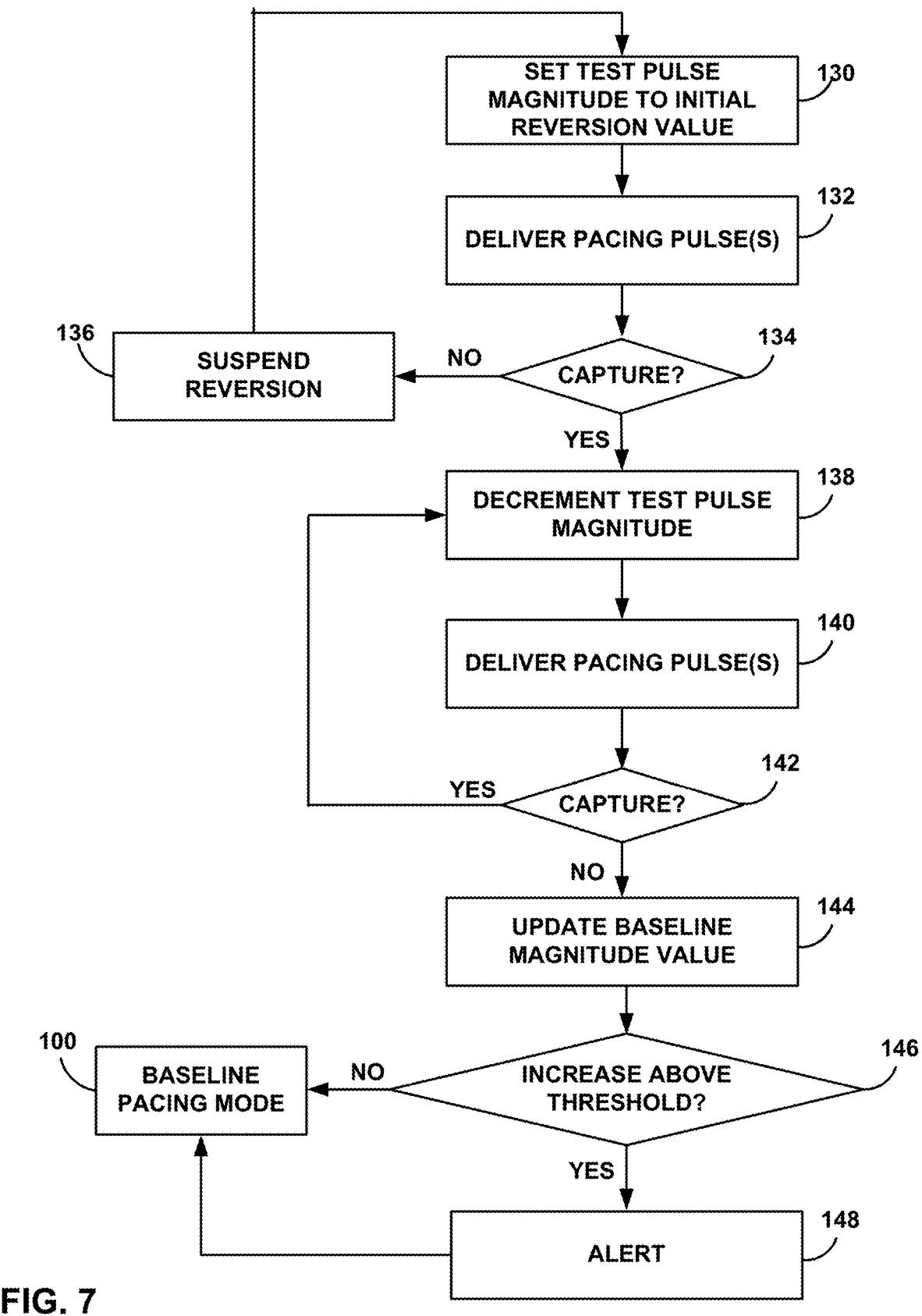
FIG. 7 is a flow diagram illustrating an example technique for reverting from a post-shock pacing mode to a baseline pacing mode.

FIG. 5 is a flow diagram illustrating an example technique for transitioning from a baseline pacing mode to a post-shock pacing mode in response to determining that an anti-tachyarrhythmia shock was delivered, and reverting from the post-shock pacing mode to the baseline pacing mode. The flowchart of FIGS. 5-7 are intended to illustrate the functional operation of IPD 16, medical systems 8a and 8b, and other devices and systems described herein, and should not be construed as reflective of a specific form of software or hardware necessary to practice the methods described. Methods described in conjunction with flow diagrams presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented by processing circuitry hardware as execution of one or more software modules, which may be executed by themselves or in combination with other software.

The example methods illustrated by FIGS. 5-7 may be performed, by any one or more devices described herein, and may be performed, in part, by processing circuitry of any one or more devices described herein, such as by processing circuitry 80 of IPD 16, processing circuitry of ICD 9, and processing circuitry of external device 21. For ease of description, the methods of FIGS. 5-7 will be described hereafter as being performed by processing circuitry 80 of IPD 16.

According to the example method of FIG. 5, processing circuitry 80 controls therapy delivery circuitry 84 of IPD 16 to deliver pacing pulses according to a baseline pacing mode, e.g., a bradycardia pacing mode (100). The baseline pacing mode may specify a baseline value of a pacing pulse magnitude. e.g., pulse amplitude and/or pulse width.

The processing circuitry 80 determines whether an anti-tachyarrhythmia shock was delivered to patient 14 (102). For example, shock detection circuitry 88 may detect a shock delivered by another medical device, such as extracardiovascular ICD system 30a or 30b, based on an electrical signal sensed by sensing circuitry 86 via electrodes 52 and 60, as described herein. In some examples, processing circuitry 80 determines that the shock was delivered, without detecting the shock itself, by detecting asystole, as described herein. In some examples, processing circuitry 80 detects a tachyarrhythmia of heart 26, e.g., based on the electrical signal sensed by sensing circuitry 86 via electrodes 52 and 60, and determines whether an anti-tachyarrhythmia shock was delivered to patient 14 within a predetermined interval beginning at the detection of the tachyarrhythmia. In examples in which an IMD that delivers anti-tachyarrhythmia shocks performs the example method of FIG. 5, the IMD will know when it has delivered a shock.

Processing circuitry 80 may continue to control therapy delivery circuitry 84 to deliver pacing pulses according to the baseline pacing mode until processing circuitry 80 determines that a shock was delivered (NO of 102). In response to determining that a shock was delivered (YES of 102), processing circuitry 80 controls therapy delivery circuitry 84 to deliver post-shock pacing according to a post shock pacing mode, as described herein (104). After delivery of post-shock pacing, processing circuitry 80 may revert IPD 16 to the baseline pacing mode (106).

FIG. 6 is a flow diagram illustrating an example technique for determining whether an anti-tachyarrhythmia shock was delivered. The example technique described in FIG. 6 may be used, for example, by IPD 16 in block 102 of FIG. 5. In some examples, processing circuitry 80 detects a tachyarrhythmia of heart 26, e.g., based on the electrical signal sensed by sensing circuitry 86 via electrodes 52 and 60, and, in response the detection of the tachyarrhythmia, determines whether an anti-tachyarrhythmia shock was delivered according to the example technique of FIG. 6.

In other examples, the technique described in FIG. 6 may be employed by any medical device to determine that another medical device delivered an anti-tachyarrhythmia shock based on either detecting the shock itself or, if the shock is not (e.g., cannot be) detected, detecting asystole of heart 26. The example technique described in FIG. 6 may be performed by the medical device for any purpose. For example, a medical device performing the example technique of FIG. 6 need not deliver cardiac pacing according to a baseline pacing mode (100 of FIG. 5) prior to determining whether a shock was delivered, deliver post-shock pacing according to a post-shock pacing mode in response to determining that the shock was delivered (104 of FIG. 5), or deliver any cardiac pacing or other therapy.

According to the example of FIG. 6, sensing circuitry 86 senses an electrical signal via electrodes 52 and 60 (110). The electrical signal may include the electrical activity, e.g., depolarizations, of heart 26, as well as any other signal across electrodes 52 and 60, such as those caused by delivery of an anti-tachyarrhythmia shock to patient 14. Processing circuitry 80 determines whether an amplitude of the signal, such as an amplitude of a derivative of the signal (e.g., first derivative indicating slope), is above a shock threshold (112). If the amplitude is above the shock threshold (YES of 112), processing circuitry 80 detects an anti-tachyarrhythmia shock delivered by another medical device, e.g., extracardiovascular ICD system 30a or 30b (114).

Processing circuitry 80 is also configured, e.g., when the amplitude of the signal is not above the shock threshold (NO of 112), to determine whether asystole of heart 26 is detected based on the electrical signal, e.g., based on the absence of cardiac depolarizations in the signal, as described herein (116). Processing circuitry 80 may be configured to detect asystole (YES of 116) if sensing circuitry 86 has not indicated detection of a cardiac depolarization for at least an asystole threshold period of time. Processing circuitry 80 may implement an asystole timer, which may begin and/or be reset upon detection of tachyarrhythmia, termination of ATP, or detection of a cardiac depolarization, as examples. Processing circuitry 80 may detect asystole when a value of the timer meets and/or exceeds the asystole threshold. In response to detecting asystole (YES of 116), processing circuitry 80 determines that the other medical device delivered an anti-tachyarrhythmia shock (118). Absent detection of asystole (NO of 116), processing circuitry 80 may continue to monitor the sensed electrical signal (110).

FIG. 7 is a flow diagram illustrating an example technique for reverting from a post-shock pacing mode to a baseline pacing mode. The example technique described in FIG. 7 may be used, for example, by IPD 16 in block 106 of FIG. 5. In other examples, the technique described in FIG. 7 may be employed by any medical device to revert from a post-shock pacing mode to a baseline, e.g., bradycardia, pacing mode. For example, the technique described in FIG. 7 may be employed by an ICD configured to deliver both cardiac pacing and anti-tachyarrhythmia shock therapies, such as an extracardiovascular ICD system, or an ICD coupled to intracardiac leads. The like-numbered block in FIG. 7 is described above in further detail with reference to FIG. 5.

According to the example technique of FIG. 7, processing circuitry 80 controls IPD 16 to deliver pacing pulse to iteratively test decreasing values of pacing pulse magnitude to identify a capture threshold of heart 26. As illustrated by the example of FIG. 7, processing circuitry sets an initial test pulse magnitude for one or more test pacing pulses delivered by IPD 16 to an initial reversion value, which is greater than a baseline value, but less than a post-shock pacing value, of the pacing pulse magnitude (130). Processing circuitry 80 controls therapy delivery circuitry 84 to deliver one or more test pacing pulses at the initial reversion pulse magnitude value (132). In some examples, as described in greater detail above, the one or more test pacing pulses at the initial reversion pulse magnitude value may be preceded and/or followed by support pacing pulses at a higher pulse magnitude value, such as the post-shock value of pacing pulse magnitude. Processing circuitry 80 determines whether the one or more pulses at the initial reversion value captured heart 26 (134).

If the one or more pulses at the initial reversion value failed to capture heart 26 (NO of 134), processing circuitry 80 suspends the reversion to the baseline pacing mode (136). As described above, suspending the reversion may include delivering one or more additional pulses at the post-shock pacing value of the pulse magnitude prior to re-starting the reversion from the post-shock pacing mode to the baseline pacing mode.

If the one or more pulses at the initial reversion value captured heart 26 (YES of 134), processing circuitry 80 decrements the test pulse magnitude (138), and controls therapy delivery circuitry 84 to deliver one or more test pacing pulse at the decremented test magnitude value (140). Processing circuitry 80 determines whether the one or more test pulses at the decremented magnitude value captured heart 26 (142). Processing circuitry 80 may iteratively decrement the test magnitude value (138), and control delivery of the one or more test pacing pulses at the decremented magnitude value (140), so long as the decremented test magnitude values capture heart 26 (YES of 142). In some examples, as described in greater detail above, the one or more test pacing pulses at the decremented pulse magnitude value may be preceded and/or followed by support pacing pulses at a higher pulse magnitude value, such as the previous test pulse magnitude value.

In response to determining that one or more of the pacing pulses having a decremented test magnitude fails to capture heart 26 (NO of 142), processing circuitry 80 updates the baseline pacing pulse magnitude value for the baseline pacing mode (144). For example, processing circuitry 80 may update the baseline value to be a predetermined or programmable margin above the magnitude that preceded the magnitude that failed to capture heart 26.

In some examples, as illustrated in FIG. 7, processing circuitry 80 determines whether updating the baseline value of pacing pulse magnitude resulted in an increase of the baseline value by at least a threshold amount (146). If the baseline value increased by at least the threshold amount (YES of 146), processing circuitry may provide an alert, e.g., store a flag in memory 82 and/or provide an alert to external device 21 or another computing device or system via communication circuitry 94 (148). Whether or not the baseline value increased by at least the threshold amount, processing circuitry 80 controls therapy delivery circuitry 84 to deliver pacing pulses having the updated baseline value of the pacing pulse magnitude according to the baseline pacing mode (100).

The baseline value having increased by at least the threshold may indicate a pacing threshold change due to the tachyarrhythmia, or delivery of anti-tachyarrhythmia therapies in response to the tachyarrhythmia. A clinician may consider such a change clinically significant, and providing the alert when the baseline value increased by at least the threshold amount may inform the clinician of such a change. The increased baseline value of pacing magnitude may also impact the useful life of a power source of IPD 16, and the alert may notify the clinician of this possibility.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method comprising:
   sensing, by an implantable medical device, an electrical signal via a plurality of electrodes;
   detecting, by the implantable medical device, a tachyarrhythmia of a heart based on the electrical signal;
   detecting, by the implantable medical device, asystole of the heart based on the electrical signal;
   determining, by the implantable medical device, that the detection of asystole was within a threshold period of time from the detection of the tachyarrhythmia; and
   determining, by the implantable medical device, that the detection of asystole is indicative of delivery of an anti-tachyarrhythmia shock based on the determination that the detection of asystole was within the threshold period of time from the detection of the tachyarrhythmia.

2. The method of claim 1, wherein detecting asystole comprises determining that a length of time without sensing a depolarization of the heart within the electrical signal exceeds an asystole threshold.

3. The method of claim 1, wherein the implantable medical device comprises an intracardiac pacing device comprising a housing and the plurality of electrodes configured for implantation in the heart, the housing containing therapy delivery circuitry configured to generate the pacing pulses for delivery via the plurality of electrodes.

4. A method comprising:
sensing, by an implantable medical device, an electrical signal via a plurality of electrodes;
delivering pacing pulses to the heart according to a plurality of intervals;
detecting, by the implantable medical device, a tachyarrhythmia based on the electrical signal;
detecting, by the implantable medical device, asystole of a heart based on the electrical signal;
determining, by the implantable medical device, that the detection of asystole was within a threshold period of time from the detection of the tachyarrhythmia; and
withholding, by the implantable medical device, delivery of the pacing pulses for one or more of the plurality of intervals based on the determination that the detection of asystole was within a threshold period of time from the detection of the tachyarrhythmia.

5. The method of claim 1,
wherein determining that the detection of asystole is indicative of delivery of the anti-tachyarrhythmia shock comprises determining that the detection of asystole is indicative of delivery of a first anti-tachyarrhythmia shock, and
wherein the method further comprises:
determining, by the implantable medical device, that an amplitude of the electrical signal is above an anti-tachyarrhythmia shock threshold; and
detecting, by the implantable medical device, delivery of a second anti-tachyarrhythmia shock based on the determination that the amplitude of the electrical signal is above the anti-tachyarrhythmia shock threshold.

6. The method of claim 5, wherein determining that the amplitude of the electrical signal is above the anti-tachyarrhythmia shock threshold comprises at least one of:
detecting DC voltage polarization across the plurality of electrodes; or
detecting a change in the amplitude at or greater than the anti-tachyarrhythmia shock threshold.

7. The method of claim 5, further comprising:
delivering first post-shock pacing in response to the determination that the detection of asystole is indicative of delivery of the first anti-tachyarrhythmia shock; and
delivering second post-shock pacing in response to the detection of delivery of the second anti-tachyarrhythmia shock.

8. The method of claim 1, further comprising delivering post-shock pacing in response to the determination that the detection of asystole is indicative of delivery of an anti-tachyarrhythmia shock.

9. An implantable medical device comprising:
sensing circuitry configured to sense an electrical signal via a plurality of electrodes; and
processing circuitry configured to:
detect a tachyarrhythmia of a heart based on the electrical signal;
detect asystole of the heart based on the electrical signal;
determine that the detection of asystole was within a threshold period of time from the detection of the tachyarrhythmia; and
determine that the detection of asystole is indicative of delivery of an anti-tachyarrhythmia shock based on the determination that the detection of asystole was within the threshold period of time from the detection of tachyarrhythmia.

10. The implantable medical device of claim 9, wherein the processing circuitry is configured to detect asystole by at least determining that a length of time without sensing a depolarization of the heart within the electrical signal exceeds an asystole threshold.

11. The implantable medical device of claim 9,
wherein the implantable medical device further comprises therapy delivery circuitry configured to deliver pacing pulses to the heart according to a plurality of intervals, and
wherein the processing circuitry is further configured to control the therapy delivery circuitry to withhold the delivery of the pacing pulses for one or more of the plurality of intervals based on the determination that the detection of asystole is indicative of delivery of an anti-tachyarrhythmia shock.

12. The implantable medical device of claim 9,
wherein the implantable medical device further comprises therapy delivery circuitry configured to deliver post-shock pacing pulses to the heart, and
wherein the processing circuitry is further configured to control the therapy delivery circuitry to deliver the post-shock pacing pulses in response to the determination that the detection of asystole is indicative of delivery of the anti-tachyarrhythmia shock.

13. The implantable medical device of claim 12, wherein the implantable medical device comprises an intracardiac pacing device further comprising a housing configured for implantation in the heart and the plurality of electrodes configured for implantation in the heart, the housing containing the therapy delivery circuitry, the sensing circuitry, a memory operably coupled to the processing circuitry, and the processing circuitry.

14. The implantable medical device of claim 9,
wherein to determine that the detection of asystole is indicative of delivery of the anti-tachyarrhythmia shock, the processing circuitry is configured to determine that the detection of asystole is indicative of delivery of a first anti-tachyarrhythmia shock, and
wherein the processing circuitry is further configured to:
determine that an amplitude of the electrical signal is above an anti-tachyarrhythmia shock threshold; and
detect delivery of a second anti-tachyarrhythmia shock based on the determination that the amplitude of the electrical signal is above the anti-tachyarrhythmia shock threshold.

15. The implantable medical device of claim 14, wherein to determine that the amplitude of the electrical signal is above the anti-tachyarrhythmia shock threshold, the processing circuitry is configured to at least one of:
detect DC voltage polarization across the plurality of electrodes; or
detect a change in the amplitude at or greater than the anti-tachyarrhythmia shock threshold.

16. An implantable medical device comprising:
therapy delivery circuitry configured to deliver pacing pulses to a heart of a patient via a plurality of electrodes;
sensing circuitry configured to sense an electrical signal via the plurality of electrodes;
a memory configured to store:
a baseline value of a pacing pulse magnitude for delivery of pacing pulses according to a baseline pacing mode;
a post-shock value of the pacing pulse magnitude for delivery of pacing pulses according to a post-shock pacing mode, wherein the post-shock value of the pacing pulse magnitude is greater than the baseline value; and an initial reversion value of the pacing pulse magnitude that is greater than the baseline value and less than the post-shock value; and processing circuitry configured to:
control the therapy delivery circuitry to deliver pacing pulses having the baseline value of the pacing pulse magnitude according to the baseline pacing mode;
determine that an amplitude of the electrical signal is above an anti-tachyarrhythmia shock threshold;
detect delivery of an anti-tachyarrhythmia shock by another medical device based on the determination;
detect asystole of the heart based on the electrical signal;
determine, without detecting the delivery of the anti-tachyarrhythmia shock, that the other medical device delivered the anti-tachyarrhythmia shock based on the detection of asystole;
in response to either detecting the delivery of the anti-tachyarrhythmia shock by another medical device or determining, without detecting the delivery of the anti-tachyarrhythmia shock, that the other medical device delivered the anti-tachyarrhythmia shock, control the therapy delivery circuitry to switch to delivery of pacing pulses having the post-shock value of the pacing pulse magnitude according to the post-shock pacing mode; and
revert the implantable medical device from the post-shock pacing mode to the baseline pacing mode by at least:
controlling the therapy delivery circuitry to deliver a plurality of pacing pulses to the heart to iteratively test a plurality of values of the pacing pulse magnitude that decrease from the initial reversion value;
determining whether each of the plurality of values of the pacing pulse magnitude captured the heart; and
in response to determining that one of the plurality of values of the pacing pulse magnitude failed to capture the heart:
updating the baseline value of the pacing pulse magnitude; and
controlling the therapy delivery circuitry to deliver pacing pulses having the updated baseline value of the pacing pulse magnitude according to the baseline pacing mode.

* * * * *